(12) United States Patent
Odar et al.

(10) Patent No.: US 8,703,122 B2
(45) Date of Patent: *Apr. 22, 2014

(54) METHOD FOR DIRECTED CELL IN-GROWTH AND CONTROLLED TISSUE REGENERATION IN SPINAL SURGERY

(75) Inventors: Johann Odar, Muehlausen (DE); Raymond Nistor-Gallo, Baden (AT)

(73) Assignees: Baxter International Inc., Deerfield, IL (US); Baxter Healthcare S.A., Deerfield, IL (US)

( * ) Notice: Subject to any disclaimer, the term of this patent is extended or adjusted under 35 U.S.C. 154(b) by 713 days.

This patent is subject to a terminal disclaimer.

(21) Appl. No.: 12/302,716

(22) PCT Filed: May 30, 2007

(86) PCT No.: PCT/EP2007/004791
§ 371 (c)(1),
(2), (4) Date: Jul. 2, 2009

(87) PCT Pub. No.: WO2007/137839
PCT Pub. Date: Dec. 6, 2007

(65) Prior Publication Data
US 2010/0028309 A1 Feb. 4, 2010

Related U.S. Application Data

(60) Provisional application No. 60/809,591, filed on May 31, 2006.

(51) Int. Cl.
*A61K 35/12* (2006.01)
*C12N 11/02* (2006.01)

(52) U.S. Cl.
USPC .......................................... 424/93.7; 435/177

(58) Field of Classification Search
USPC .......................................... 424/93.7; 435/177
See application file for complete search history.

(56) References Cited

U.S. PATENT DOCUMENTS

| | | |
|---|---|---|
| 2,507,244 A | 5/1950 | Correll |
| 2,558,395 A | 6/1951 | Studer |
| 4,013,078 A | 3/1977 | Field |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,424,208 A | 1/1984 | Wallace et al. |
| 4,453,939 A | 6/1984 | Zimmerman et al. |
| 4,482,386 A | 11/1984 | Wittwer et al. |
| 4,515,637 A | 5/1985 | Cioca |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,891,359 A | 1/1990 | Saferstein et al. |
| 4,925,677 A | 5/1990 | Feijen |
| 4,946,870 A | 8/1990 | Partain, III et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |

(Continued)

FOREIGN PATENT DOCUMENTS

| | | |
|---|---|---|
| EP | 0132983 A | 2/1985 |
| EP | 0376931 | 7/1990 |

(Continued)

OTHER PUBLICATIONS

Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).
Baxter product brochure for TissuFleece E, TissuCone E and TissuFoil E (2003).
Baxter Product Catalogue; Collagen; 4 pages (2006).
Chaplin, J.M., et al.; "Use of an Acellular Dermal Allograft for Dural Replacement: An Experimental Study"; Neurosurgery: vol. 45:2; pp. 320-327 (Aug. 1999).
Collins, Ronald et al., "Use of Collagen Film as a Dural Substitute: Preliminary Animal Studies", Journal of Biomedical Materials Research, vol. 25, 267-276 (1991).
Filippi, R., et al.; "Bovine Pericardium for Duraplasty: Clinical Results in 32 Patients"; Neurosurg. Rev.; vol. 20; pp. 103-107 (2001).
Hieb, Lee D. et al., "Spontaneous Postoperative Cerebrospinal Fluid Leaks Following Application of Anti-Adhesion Barrier Gel", SPINE vol. 26, No. 7, pp. 748-751, 2001.

(Continued)

*Primary Examiner* — Marcia S Noble
(74) *Attorney, Agent, or Firm* — Kilpatrick Townsend & Stockton LLP

(57) ABSTRACT

The present invention relates to a method for directed cell in-growth and controlled tissue regeneration to prevent postsurgical or post-traumatic adhesion and fibrosis formation on the injured surface of a tissue selected from the group consisting of spinal column tissue, dura mater, and spinal nerves in a mammal, comprising the step of providing, covering and separating the tissue with a bioactive biofunctional, nonporous, microscopically multilayered collagen foil biomatrix, and to a method for treating a defect in a mammal comprising the step of providing, covering and separating said tissue with a bioactive biofunctional, non-porous, microscopically multilayered collagen foil biomatrix.

26 Claims, 20 Drawing Sheets

(56) References Cited

U.S. PATENT DOCUMENTS

| | | |
|---|---|---|
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,853,749 A | 12/1998 | Hobbs |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,959,735 A | 9/1999 | Maris et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A | 12/2000 | Rhee et al. |
| 6,179,872 B1 | 1/2001 | Bell et al. |
| 6,227,394 B1 | 5/2001 | Shinoda |
| 6,312,474 B1 | 11/2001 | Francis et al. |
| 6,312,725 B1 | 11/2001 | Wallace et al. |
| 6,328,229 B1 | 12/2001 | Duronio et al. |
| 6,440,167 B2 | 8/2002 | Shimizu |
| 6,458,386 B1 | 10/2002 | Schacht et al. |
| 6,458,889 B1 | 10/2002 | Trollsas et al. |
| 6,624,245 B2 | 9/2003 | Wallace et al. |
| 6,706,690 B2 | 3/2004 | Reich et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 2001/0016205 A1 | 8/2001 | Shimizu |
| 2002/0193448 A1 | 12/2002 | Wallace et al. |
| 2003/0064109 A1 | 4/2003 | Qian et al. |
| 2005/0142162 A1 | 6/2005 | Hunter et al. |
| 2006/0147492 A1 | 7/2006 | Hunter et al. |
| 2006/0167561 A1 | 7/2006 | Odar et al. |
| 2008/0085316 A1 | 4/2008 | Qian et al. |
| 2008/0091277 A1 | 4/2008 | Deusch et al. |
| 2008/0286376 A1 | 11/2008 | Qian et al. |
| 2009/0142396 A1 | 6/2009 | Odar et al. |
| 2010/0292717 A1 | 11/2010 | Petter-Puchner et al. |
| 2010/0318048 A1 | 12/2010 | Hoefinghoff et al. |

FOREIGN PATENT DOCUMENTS

| | | |
|---|---|---|
| EP | 0132983 B2 | 6/1991 |
| EP | 0493387 | 7/1992 |
| EP | 0781564 A2 | 7/1997 |
| EP | 0891193 | 1/1999 |
| EP | 0612252 B1 | 5/1999 |
| EP | 1084720 A1 | 3/2001 |
| EP | 1283063 A1 | 2/2003 |
| EP | 1484070 A1 | 12/2004 |
| EP | 01414370 B1 | 4/2007 |
| JP | 59-113889 | 6/1984 |
| JP | 05308969 | 11/1993 |
| JP | 6-254148 | 9/1994 |
| JP | 9-504719 | 5/1997 |
| JP | 07090241 | 4/2007 |
| KR | 10-1991-0007847 B1 | 10/1991 |
| WO | WO 86/00912 | 2/1986 |
| WO | WO 92/21354 | 12/1992 |
| WO | WO 94/27630 A1 | 12/1994 |
| WO | WO 95/12371 | 5/1995 |
| WO | WO 92/22252 | 6/1995 |
| WO | WO 95/15747 | 6/1995 |
| WO | WO 96/04025 | 2/1996 |
| WO | WO 96/06883 | 3/1996 |
| WO | WO 96/10374 | 4/1996 |
| WO | WO 96/10428 | 4/1996 |
| WO | WO 96/14368 | 5/1996 |
| WO | WO 96/39159 | 12/1996 |
| WO | WO 97/37694 A1 | 10/1997 |
| WO | WO 98/08550 A1 | 3/1998 |
| WO | WO 99/13902 A1 | 3/1999 |
| WO | WO 02/22184 A2 | 3/2002 |
| WO | WO 02-070594 A2 | 9/2002 |
| WO | WO 03/007845 A1 | 1/2003 |
| WO | WO 2004/108179 A1 | 12/2004 |
| WO | WO 2006/031358 A | 3/2006 |
| WO | WO 2006/118460 A1 | 11/2006 |
| WO | WO 2007/001926 A2 | 1/2007 |
| WO | WO 2007/137839 A2 | 12/2007 |
| WO | WO 2007/137839 A3 | 12/2007 |
| WO | WO 2008/016983 A2 | 2/2008 |

OTHER PUBLICATIONS

Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.

Kline, D.G.; "Dural Replacement with Resorbable Collagen"; Arch Surg; vol. 91; pp. 924-929 (Dec. 1965).

Kuhn, J. et al., "Bilateral Subdural Haemotomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.

Laquerriere, A., et al.; "Experimental Evaluation of Bilayered Human Collagen as a Dural Substitute"; J. Neurosurg; vol. 78; pp. 487-491 (Mar. 1993).

(56) References Cited

OTHER PUBLICATIONS

Le, Anh X. et al., "Unrecognized Durotomy After Lumbar Discectomy: A Report of Four Cases Associated with the Use of ADCON-L", SPINE vol. 26, No. 1, pp. 115-118, 2001.
Lee, J.F., et al.; "Experimental Evaluation of Silicone-Coated Dacron and Collagen Fabric-Film Laminate as Dural Substitutes"; J. Neurosurg.; vol. 27; pp. 558-564 (Apr. 1967).
Matsumoto, K., et al.; "A Gelatin Coated Collagen-Polyglycolic Acid Composite Membrane as a Dural Substitute"; ASAIO Journal; pp. 641-645 (2001).
Maurer, P.K., et al.; "Vicryl (Polyglactin 910) Mesh as a Dural Substitute"; J Neurosurg; vol. 63; pp. 448-452 (Sep. 1985).
Meddings, N., et al.; "Collagen Vicryl—A New Dural Prosthesis"; Acta Neurochir; vol. 117; pp. 53-58 (1992).
Mello, L.R., et al.; "Duraplasty with Biosynthetic Cellulose: An Experimental Study"; J Neurosurg; vol. 86; pp. 143-150 (Jan. 1997).
Narotam, P.K., et al.; "A Clinicopathological Study of Collagen Sponge as a Dural Graft in Neurosurgery"; J Neurosurg; vol. 82; pp. 406-412 (Mar. 1995).
Narotam, P.K., et al.; "Experimental Evaluation of Collagen Sponge as a Dural Graft"; British Journal of Neurosurgery; vol. 7; pp. 635-641 (1993).
O'Neill, P., et al.; "Use of Porcine Dermis as Dural Substitute in 72 Patients"; J. Neurosurg.; vol. 61; pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; Acta Neurochir; vol. 139; pp. 827-838 (1997).
Park, Y-K., at al.; "Prevention of Arachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
Pietrucha, K.; "New Collagen Implant as Dural Substitute"; Biomatarials; vol. 12; pp. 320-323 (Apr. 1991).
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al.; "Utilisation du Polyester Urethane (Neuro-Patch®) Comme Substitut Dural"; Neurochirugie; vol. 49:2-3; pp. 83-89 (2003).
Reddy, M., et al.; "A Clinical Study of a Fibrinogen-Based Collagen Fleece for Dural Repair in Neurosurgery"; Acta Neurochir; vol. 144; pp. 265-269 (2002).
Ross, Jeffrey S. et al., "Association Between Peridural Scar and Recurrent Radicular Pain After Lumbar Discectomy: Magnetic Resonance Evaluation", Neurosurgery, pp. 855-863, 1996.
San-Galli, F., et al.; "Experimental Evaluation of a Collagen-Coated Vicryl Mesh as a Dural Substitute"; Neurosurgery: vol. 30:3; pp. 396-401 (1992).
Shaffrey, C.I., et al.; "Neurosurgical Applications of Fibrin Glue: Augmentation of Dural Closure in 134 Patients"; Neurosurgery; vol. 26:2; pp. 207-210 (1990).
Smith, KA, et al.; "Delayed Postoperative Tethering of the Cervical Spinal Corei"; J Neurosurg; vol. 81; pp. 196-201 (Aug. 1994).
Vinas, F.E., et al.; "Evaluation of Expanded Polytetrafluoroethylene (ePTFE) versus Polydioxanone (PDS) for the Repair of Dura Mater Defects"; Neurological Research; vol. 21; pp. 262-268 (Apr. 1999).
Warren, W.L., et al.; Dural Repair Using Acellular Human Dermis: Experience with 200 Cases: Technique Assessment; Neurosurgery; vol. 46:6; pp. 1391-1396 (Jun. 2000).
Ziegelaar, B.W.; "Tissue Engineering of a Tracheal Equivalent", Doctoral Thesis at Ludwig Maximilians University, Munich, Germany; 25 pages (2004).
T. Kofidis et al., "Clinically established Hemostatis Scaffold (Tissue Fleece) as Biomatrix in Tissue-and organ-engineering research", Tissue Eng vol. 9, No. 3, 2003, S.517-523; ISSN: 1076-3279.
Knopp U., "A new collagen foil versus a cadaveric dura graft for dural defects—a comparative animal experimental study", EANS—12th European Congress of Neurosurgery, Lisbon, Sep. 7-12, 2003, 663-666.
Ziegelaar, BW et al., "The characterisation of human respiratory epithelial cells cultured on reabsorbable scaffolds: first steps towards a tissue engineered tracheal replacement", Biomaterials 23 (2002), 1425-1438; ISSN 0142-9612.
GentaFleece Kollagenvlies Version 5 found on internet at: http://www.advancingbiosurgery.com/en_EU/downloads/ifu_gentafleece.pdf, Mar. 2002, 2 pages.
GentaFleece Kollagenvlies Version 5 found on internet on Jan. 11, 2010 at: http://www.baxterbiosurgery.com/en_EU/downloads/ifu_gentafleece.pdf, Apr. 16, 2002, 6 pages, *English portion of instructions for use*.
Raul, J.S., et al.; "Utilisation du Polyester Urethane (Neuro-Patch®) Comme Substitut Dural"; Neurochirugie; vol. 49:2-3; pp. 83-89 (2003), English abstract only on p. 83.
Springorum, H.W.; "Die Verwendung von Kollagenfolien zur Uberbruckung von Defekten des Gleitgewebes bei Achillotenotomien und Achillessehnenrupturen"; Akt. Traumatal!.; vol. 15; pp. 120-121 (1985), English abstract only on p. 120.
Stricker, A., et al.; "Die Verwendung von TissuFoil Membran bei der Sinusbodenaugmentation"; Ellipse; vol. 17:1; pp. 1-5 (2001), English abstract only on p. 1.
TissuFleece E, Version 5, found on internet on Jan. 11, 2010 at: http://tissuesealing.com/en_EU/downloads/ifu_tissufleece.pdf, Nov. 25, 2003, 6 pages, *English portion of instructions for use*.
Ansell et al., "Gelfoam and Autologous Clot Embolization: Effect on Coagulation", *Invest. Radiol.* (1978) 13:115-120.
Barton et al., "Fibrin Glue as a Biologic Vascular Patch—A Comparative Study" (abstract posted at http://www.ncbi.nlm.nih.gov/ on Jan. 3, 2001 from) *J. Surg. Res.* (1986) 40(5): 510-513.
Boyers et al., "Reduction of Postoperative Pelvic Adhesions in the Rabbit with Gore-Tex Surguical Membrane" *Fert. Ster.* (1988) 49(6):1066-1070.
Bruck, S. D., Ed., Controlled Drug Delivery, CRC Press, Boca Raton, FL (1983) A title page and table of contents.
Cantor et al., "Gelfoam and Thrombin in Gastrointestinal Bleeding: An Experimental Study", pp. 890-893.
Cantor et al., "Gelfoam and Thrombin in Treatment of Massive Gastroduodenal Hemmorhage: A Preliminary Report" *Am J. Surg.* (1950) pp. 883-887.
Cantor et al., "Gelfoam and Thrombin in Treatment of Massive Upper Gastroduodenal Hemorrhage", *Am. J. Surg.* (1951) pp. 230-235.
Chuang et al., "Sheath Needle for Liver Biopsy in High-Risk Patients", *Radiology* (1988) 166:261-262.
Collins et al., "Enemata of Gelfoam—Milk Suspension Combined with Thrombin Solution to Control Massive Hemorrhage Following Anorectal Surgery", *Am. J. Proctol.* (1951) 2:60-63.
Edgerton et al., "Vascular Hamartomas and Hemangiomos: Classification and Treatment" *Southern Med. J.* (1982) 75(12):1541-1547.
Heller et al., "Release of Norethindrone from Poly(Ortho Esters)" *Polymer Engineering Sci.* (1981) 21:727-731.
Hood et al., "Efficacy of Topical Hemostat Floseal Matrix in Vascular Surgery," 24th World Congress of the International Society for Cardiovascular Surgery (Sep. 12-16, 1999), 2 pages total.
Hotz et al., "Collagen and Fibrin as Biologic Binders from Granular Hydroxyapatite" (abstract posted at http://www.ncbi.nlm.nih.gov/ on Jan. 3, 2001 from) *Dtsh. Z. Mund. Kiefer Geichtshir.* (1989) 13(4):296-300.
Jeong et al., "Biodegradable Block Copolymers as Injectible Drig-Delivery Systems" *Nature* (1997) 388:860-862.
Krill et al., "Topical Thrombin and Powdered Gelfoam: An Efficiaent Hemostatic Treatment for Surgery", *J. Tenn. Dent. Assoc.* (1986) 66(2):26-27.
Langer et al., "Chemical and Physical Structure of Polymerns as Carriers for Controlled Release of Bioactive Agents: A Review" *Rev. Marco Chem. Phys.* (1983) C23(1):61-126.
Leong et al., "Polyanhydrides for Controlled Release of Bioactive Agents" *Biomaterials* (1986) 7:364-371.
Leong et al., "Polymeric Controlled Drug Delivery" *Adv. Drug Delivery Rev.* (1987)1:199-233.

(56) References Cited

OTHER PUBLICATIONS

Maok, "Hemostatic Agents" (1991) *Today's O.R. Nurse*, pp. 6-10.
Masar et al., "Synthesis of Polyurethanes and Investigation of their Hydrolytic Stability" *J. Polymer. Sci.*, Polymer Symposium (1979) 66:259-268.
McClure et al., "Massive Gastroduodenal Hemorrhage: Treatment with Powdered Gelfoam and Buffered Thrombin Solution" *Surg.* (1952) 32:630-637.
PCT International Preliminary Report on Patentability and Written Opinion mailed Feb. 17, 2009, International Application No. PCT/US2007/074984, 8 pages.
Pitt et al., "Controlled Release of Bioactive Materials", R. Baker, Ed., Academic Press, New York, 1980.
Riley et al., "Percutaneous Liver Biopsy with Plugging of Needle Track: A Safe Method for Use in Patients with Impaired Coagulation" *Lancet* (Aug. 25, 1984) pp. 436.
Sidman et al., "Biodegradable, Implantable Sustained Release Systems Based on Glutamic Acid Copolymers" *J. Membrane Science* (1979) 7:227-291.
Sugitachi et al., "A Newly Devised Chemo-embolic Agent, G.T. XIII-ADM." (English abstract posted at http://www.ncbi.nlm.nlm.gov/ on Jan. 3, 2001 from) *Gan. To. Kagaku Ryoho.* (1985) 12(10) 1942-1943.
Sugitachi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho.* (1992) 19(10):1640-1643.
Sugitachi et al., "Preoperative Transcatheter Arterial Chemo—embolization for Locally Advanced Breast Cancer: Application for New Thrombotic Materials" *Japan J. Surg.* (1983) 13(5):456-458.
Tobin et al., "Plugged Liver Biopsy in Patients with Impaired Coagulation" *Digestive Diseases and Science* (1989) 34(1):13-15.
Tucker et al., "Absorbable Gelatin (Gelfoam) Sponge" Charles T. Thomas, Publisher, Springfiled, Illinois, 3-125.
Vander Salm et al., "Reduction of Sternal Infection by Application of Topical Vancomycin" *J. Thorac. Surg.* (1989) 98:618-622.
Yuki et al., "Effects of EndoscopicVariceal Sclerotherapy using GT XIII on Blood Coagulation Tests and the Renal Kallikrein-kinin System" (English abstract posted at http://www.ncbi.nlm.nih.gov/ on Jan. 3, 2001 from) Gastroentral. Japan (1990) 25(5):561-567.
Zins et al., "US-Guided Percutaneous Liver Biopsy with Plugging of the Needle Track: A Prospective Study in 72 High-Rish Patients" *Radiology* (1992) 184(3):841-843.
Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.
Jonas, Richard A., et al., "A new sealant for knitted Dacron prostheses: Minimally cross-linked gelatin", J. Vasc. Surg., Mar. 1988;7(3), pp. 414-419.
Larson, Paul O., "Topical Hemostatic Agents for Dermatologic Surgery", J. Dermatol. Surg. Oncol., Jun. 1988;14(6), pp. 623-632.
McPherson, J. M. et al., "An examination of the biologic response to injectable, glutaraldehyde cross-linked collagen implants", J. Biomed. Mater. Res., Jan. 1986;20(1), pp. 93-107.
McPherson, J. M., et al., "The preparation and physiochemical characterization of an injectable form of reconstituted, glutaraldehyde cross-linked, bovine corium collagen", J. Biomed. Mater. Res., Jan. 1986; 20(1), pp. 79-92.
McPherson, John M., et al., "The Effects of Heparin on the Physiochemical Properties of Reconstituted Collagen", Coll. Relat. Res., Jan. 1988;8(1), pp. 65-82.
Nimni, M. E., et al., "Chemically modified collagen: A natural biomaterial for tissue replacement", J. Biomed. Mater. Res., Jun. 1987;21(6), pp. 741-771.
Nimni, Marcel E., "The cross-linking and structure modification of the collagen matrix in the design of cardiovascular prosthesis", J. of Cardiac Surgery, Dec. 1988;3(4), pp. 523-533.
Rosenblatt, Joel, et al., "Effect of electrostatic forces on the dynamic rheological properties of injectable collagen biomaterials", Biomaterials, 1992;13(12), pp. 878-886.
Rosenblatt, Joel, et al., "Injectable collagen as a pH-sensitive hydrogel", Biomaterials, Oct. 1994;15(12), pp. 985-995.
Rossler, B., et al., "Collagen microparticles: preparation and properties", J. Microencapsulation, Jan.-Feb. 1995;12(1), pp. 49-57.
Wallace, Donald G., et al., "Injectable cross-linked collagen with improved flow properties", J. of Biomedical Materials Research, Aug. 1989;23(8), pp. 931-945.
Wallace, Donald, "The relative contribution of electrostatic interactions to stabilization of collagen fibrils", Biopolymers, May-Jun. 1990; 29(6-7), pp. 1015-1026.

METHOD FOR DIRECTED CELL IN-GROWTH AND CONTROLLED TISSUE REGENERATION IN SPINAL SURGERY

FIELD OF THE INVENTION

The present invention relates to a method for preventing post-surgical or post-traumatic cellular adhesion on the surface of a tissue selected from spinal column tissue, dura mater and spinal nerves comprising the step of covering and separating the tissue with a multilayered bioactive and biofunctional collagen biomatrix foil, and to a method of directing cell growth and tissue repair and for treating a disorder in a mammal comprising the step of covering and separating said tissue with a multilayered collagen foil biomatrix. The methods of the present invention prevent peridural and perineural adhesion and scar tissue formation by providing a biofunctional matrix for directed in-growth of cells and controlled tissue regeneration.

BACKGROUND OF THE INVENTION

Internal scarring, peridural and perineural fibrosis and adhesions after spinal surgery are well known and undesired side effects of said surgery. These conditions lead to a high percentage to pain, motion difficulties and often to the need for additional surgery. The use of a gel comprising carboxymethylcellulose and polyethylene oxide for the reduction of epidural adhesions after spinal surgery is disclosed in Kim et al: "Reduction in leg pain and lower-extremity weakness with Oxiplex/SP Gel for 1 year after laminectomy, laminotomy, and discectomy. Neurosurg Focus" 17(1): *Clinical Pearl* 1: 1-6, 2004); Porchet et al: "Inhibition of epidural fibrosis with ADCON-L: effect on clinical outcome one year following re-operation for recurrent lumbar radiculopathy." *Neurol Res* 21 (Suppl 1): 51-S60, (1999); and, Ross et al: "Association between peridural scar and recurrent radicular pain after lumbar discectomy: magnetic resonance evaluation. ADCON-L European Study Group." *Neurosurgery* 38:855-863, (1996). In these examples, a gel is distributed in an uncontrolled manner in the application area and once applied, the gel distribution cannot be easily manipulated or corrected. Further, these anti-adhesion gels have limited success as a barrier and have undefined layer thickness. These anti-adhesion gels have low hemostatic properties, if any at all, and provide no wound healing support functions and do not direct cell growth and tissue regeneration. There are even reports of increased rates of CSF (cerebro spinal fluid) leaks accruing in conjunction with the use of ADCON-L (Hieb, L. D. & Stevens, D. L. (2001). Spontaneous postoperative cerebrospinal fluid leaks following application of anti-adhesion barrier gel: case report and review of the literature. *Spine,* 26(7), 748-751; Kuhn, J., Hofmann, B., Knitelius, H. O., Coenen, H. H., & Bewermeyer, H. (2005). Bilateral subdural haematomata and lumbar pseudomeningocele due to a chronic leakage of liquor cerebrospinalis after a lumbar discectomy with the application of ADCON-L gel. *J Neurol Neurosurg Psychiatry,* 76(7), 1031-1033; Le, A. X., Rogers, D. E., Dawson, E. G., Kropf, M. A., De Grange, D. A., & Delamarter, R. B. (2001). Unrecognized durotomy after lumbar discectomy: a report of four cases associated with the use of ADCON-L. *Spine,* 26(1), 115-7; discussion 118.)

One commercially available anti-adhesion product is DURAGEN PLUS. The DURAGEN PLUS barrier, which is of bovine origin, is not very shape stable, which means that its shape and position is difficult to correct after application. Further, the DURAGEN PLUS barrier does not have a high tensile strength and elasticity. And due to the fact that the DURAGEN PLUS barrier is porous it is consequently not fluid-tight (impermeable to fluids) and therefore has limited success as a barrier function. Also, DURAGEN PLUS absorbs blood which can results in fibrin bands that play a key role in the pathogenesis of adhesion formations and its porous structure promotes non-directed cell in-growth which may also contribute to uncontrolled fibrotic tissue formation and to adhesions.

Consequently, a strong need exists for a new system for directed and controlled tissue regeneration to prevent post-surgical or post-traumatic peridural and perineural adhesion formation in the tissue healing and regeneration process following surgical and traumatic injuries which does not absorb blood, which supports the remodeling, regeneration, and the wound healing process, which directs the growth and the in-growth of cells, and which acts effectively as a biofunctional separation layer.

Thus, it is an object of the present invention to provide a new method for preventing post-surgical or post-traumatic peridural or perineural adhesion and fibrosis, and directing cell in-growth and controlling tissue regeneration by using a biofunctional collagen foil matrix to cover and separate spinal column tissues.

SUMMARY OF THE INVENTION

The present invention is directed to compositions and methods of preventing post-surgical or post-traumatic peridural or perineural adhesion and fibrosis formation, directing cell growth and cell in-growth and controlling tissue regeneration after surgery or trauma by using a multilayer collagen foil biomatrix to cover and separate tissues such as spinal column tissues. Spinal column tissues include those such as spinal canal tissues, dura mater and spinal nerves. The methods of the present invention may be used, for example, during spinal surgery, in a mammal, e.g., a human being, comprising the step of covering and separating the tissue with a microscopically multilayered collagen foil biomatrix. In one example of the above method, the multilayered collagen foil biomatrix attracts cells selected from the group consisting of repair cells and regeneration cells. In another example of the above method, the multilayered structure of the biofunctional collagen foil biomatrix directs the cell growth on to the surface, and the in-growth of cells such as repair cells and regeneration cells and is remodeled to natural tissue after said in-growth and is resorbed. Further, the present invention relates to a method for treating a disorder in a mammal characterized by a defect of the spinal column tissue, comprising the step of covering and separating said tissue and/or a surrounding tissue with a multilayered collagen foil biomatrix in order to inhibit uncontrolled tissue formation.

In using collagen based compositions therapeutically, collagen based compositions are usually perceived as foreign by the host and often encapsulated. Therefore, recellularisation and remodeling to the respective anatomical tissue does not occur or is impossible, there is no directed cell in-growth and no control of the regeneration process and are merely tolerated as a "biocompatible" implant. In contrast, the multilayered collagen foil biomatrix of the present invention acts as a membrane (e.g., spinal membrane) functioning as a bioactive temporary separation layer directing cell growth within the multilayered collagen foil biomatrix and on the surface of the collagen foil biomatrix. Rather than acting solely as a barrier against cell growth, as most anti-adhesion compositions do, the multilayered collagen foil biomatrix of the present invention is extremely bioactive and supports the remodeling of the tissues. For example, two weeks after implantation, the multilayered collagen foil biomatrix of the present invention is already well integrated into the restored anatomical structure of peridural tissues. Further, during and after surgery, the nonporous, fluid-tight (e.g., blood) multilayered structure of the collagen membrane of the present invention is capable of preventing uncontrolled distribution of blood (e.g., fibrinogen/fibrin) and necrotic material from the peridural wound areas, which are responsible for supporting conditions of adhesion formation in the initial time period after surgery (in contrast to porous compositions). The collagen biomatrix of the present invention also prevents direct contact between the dura mater and the peridural wound area, the primary area of the scar formation and fibrosis. This contributes also to the controlled remodeling of anatomical structures with prevention and minimization of uncontrolled adhesion and scar formation and peridural fibrosis.

The present invention is directed in part to the following:
1. A method for directing cell growth and controlled tissue regeneration and preventing post-surgical or post-traumatic adhesion and fibrosis formation on the surface of a tissue in a mammal, comprising the steps of providing, covering and separating the tissue with a non-porous microscopically multilayered collagen foil biomatrix.
2. The method of paragraph 1 wherein the tissues are selected from the group consisting of spinal column tissue, dura mater and spinal nerves.
3. The method of paragraphs 1 or 2 wherein the cell growth is directed in the interstices between the layers of the multilayered collagen foil biomatrix.
4. The method of paragraphs 1,2 or 3 wherein the mammal is a human.
5. The method according to paragraph 2, wherein the step of covering and separating the tissue with a non-porous multilayered collagen foil biomatrix is carried out during spinal surgery.
6. The method according to paragraphs 1, 2, 3, 4 or 5 wherein the multilayered collagen foil biomatrix attracts cells selected from the group consisting of repair cells and regeneration cells.
7. The method according to paragraphs 1, 2, 3, 4 or 5 wherein the multilayered structure of the multilayered collagen foil biomatrix directs the in-growth of repair and regeneration cells within and on the surface, and within the multilayered collagen foil biomatrix.
8. The method according to paragraph 5, 6 or 7 wherein the multilayered collagen foil biomatrix is reabsorbed and remodeled to natural tissue during the in-growth of cells within a period of two to about twelve weeks post surgery.
9. The method according to paragraphs 1-8 wherein the collagen foil is derived from one of the following sources selected from the group consisting of bovine, porcine, equine, or human collagen and mixtures thereof and is attached to the tissues of the mammal using a fibrin sealant.
10. A method of preventing adhesions in mammals comprising the steps of providing, covering and separating tissue with a biofunctional, non-porous multilayered collagen foil biomatrix wherein the multilayered collagen foil has interstices between the layers for directing cell growth within and on the multilayered collagen foil biomatrix.
11. The method of paragraph 10 wherein the method prevents post-surgical adhesions and adhesions caused by trauma.
12. The method of paragraphs 10 or 11 wherein the method prevents fibrosis formation on the surface of tissues.
13. The method of paragraphs 10, 11 or 12 wherein the tissue is selected from the group consisting of spinal column tissue, dura mater, and spinal nerves.
14. The method of paragraph 10 wherein the individual layers of collagen foil are smooth and substantially non-porous.
15. The method of paragraph 14 wherein the individual layers of collagen foil are completely non-porous.
16. The method of paragraphs 10, 11 or 12 wherein the multilayered collagen foil biomatrix directs cell growth in the interstices between the layers of the multilayered collagen foil and the layers of the collagen foil are reabsorbed and remodeled into natural tissues by the host.
17. The method of paragraphs 10, 11 or 12 wherein the multilayered collagen foil acts as a temporary spinal membrane directing cell growth of new cells while preventing adhesion and fibrosis after surgery or trauma.
18. The method of paragraphs 10-17 wherein the collagen foil is derived from one of the following sources selected from the group consisting of bovine, porcine, equine, or human collagen and mixtures thereof.
19. The method of paragraph 18 wherein the collagen foil is produced recombinantly.
20. The methods of paragraphs 1, 10, 11, 12, 17 or 18 wherein the tissues are selected from the group consisting of abdominal, ovarian, pulmonary, muscle and tendon tissues.
21. The methods of paragraphs 1, 9, 10, or 18 further comprising the step of adding bioactive agents (e.g, plasminogen activators), growth factors, antibiotics, cytostatic drugs, and combinations thereof.
22. The methods of paragraph 1, 9, 10 or 18 wherein the method prevents the growth of adhesions between bone or tendon surfaces.
23. A composition for use in adhesion prevention and prevention of fibrosis formation comprising a microscopically multilayered collagen foil biomatrix wherein the multilayered collagen foil directs the growth of cells in the interstices between the collagen layers and on the outer surface of the multilayered collagen foil biomatrix.
24. The composition of paragraph 23 wherein the multilayered collagen foil biomatrix is derived from materials selected from the group consisting of bovine, porcine, equine, or human collagens.
25. The composition of paragraph 23 wherein the multilayered collagen foil biomatrix is derived from equine collagen.
26. The composition of paragraphs 23 or 25 wherein the multilayered collagen foil biomatrix's individual layers are smooth and non-porous.
27. The composition of paragraphs 23 or 25 wherein the multilayered collagen foil biomatrix's individual layers are smooth and substantially non-porous.
28. The composition of paragraph 23 or 25 wherein the layers of the multilayered collagen foil biomatrix are porous and optionally the pores are interconnected.
29. Use of a composition in the manufacture of a medicament for the prevention of adhesions and prevention of fibrosis formation in a mammal wherein the composition consists of a microscopically multilayered collagen foil biomatrix wherein the multilayered collagen foil directs the growth of repair and/or regeneration cells in the interstices between the collagen layers wherein the collagen is selected from one of the group consisting of bovine, porcine, equine, or human collagen and mixtures thereof.
30. The use of paragraph 29 wherein the adhesions are post-operative adhesions or adhesions caused by trauma such as peridural or perineural adhesions.
31. The use of paragraph 29 wherein the composition directs cell growth between the interstices of the layers.

32. The of paragraph 29 wherein the collagen foil creates a primary liquid-tight and cell-tight seal or barrier.

33. The use of paragraphs 29, 30, 31 or 32 wherein the collagen foil is attached to tissues by the use of a surgical sealant or by sutures.

34. The use of paragraphs 29-33 wherein the composition is available in kit form.

BRIEF DESCRIPTION OF THE DRAWINGS

FIG. 13 B shows a NZW rabbit 1 week postoperative; Magnification: ×20, HE staining. The figure shows the contact area between the multilayered collagen foil biomatrix and the bone at the edge of the defect (a);

FIG. 13 C shows a rabbit 1 week postoperative; Magnification: ×20; HE staining. The multilayered collagen foil biomatrix is in the center of the laminectomy defect. The multilayered collagen foil biomatrix is integrated and is separating the ventral epidural space from the dorsal scar formation;

FIG. 13 D shows a NZW rabbit 1 week postoperative; Magnification: ×2.5; HE staining. The multilayered collagen foil biomatrix is closing the laminectomy defect and separating the dura from the beginning cell rich dorsal scar formation. Cells have not penetrated the surface of the collagen biomatrix. At the edge of the collagen biomatrix beginning directed infiltration of repair cells into the multilayer structure(a);

FIG. 13 E shows a NZW rabbit 1 week postoperative; Magnification: ×2.5; HE staining. A collagen sponge (DURAGEN) was used to cover the laminectomy defect. No clear non-porous separation layer between the epidural space and the dorsal wound area. The sponge is soaked with blood;

FIG. 14 B shows a rabbit two weeks postoperative; Magnification: ×4; HE staining; the multilayered collagen foil biomatrix is fully integrated. Tissue repair cells have infiltrated the multilayer structure of the collagen biomatrix. The dura mater is separated by loose tissue with fat cells from the scar formation and the remodeled collagen biomatrix; and, FIG. 14 C shows a rabbit two weeks postoperative; Magnification: ×10; HE staining; the multilayered collagen foil biomatrix is fully integrated. Tissue repair cells have infiltrated the multilayer structure of the collagen biomatrix (a).

The dura mater is separated by loose tissue with fat cells from the scar formation and the remodeled collagen biomatrix.

DETAILED DESCRIPTION OF THE INVENTION

One aspect of the present invention relates to a method for preventing post-surgical or post-traumatic peridural or perineural adhesion and fibrosis formation on the surface of spinal column tissue, including tissues selected from the group consisting of spinal canal tissues, dura mater, and spinal nerves in a mammal, comprising the step of covering the tissue and separating the tissue from other surrounding tissues with a microscopically multilayered collagen foil biomatrix.

The multilayered collagen foil biomatrix according to the present invention is a collagenous native cross-linked microscopically multilayered biomatrix consisting of multiple layers of a substantially non-porous foil comprised of collagen fibrils in a non-naturally occurring biomatrix, e.g., as described in the international patent application WO 04/108179, the disclosure of which is herewith incorporated by reference in its entirety. The collagen foil used according to the present invention is biofunctional, bioactive, mechanically stable, elastic, non-porous and fluid-tight, especially blood and cell tight, temporary barrier against uncontrolled distribution of blood, fibrinogen, necrotic material and damaged tissues. A defined bioactive separation layer between the spinal column tissues thus initially shields the spinal column tissue and surrounding tissues, one or both of which may be abraded or otherwise damaged. The multilayered collagen foil biomatrix acts as hemostatic agent and inhibits uncontrolled fibrin bands formation and distribution as well as hematomas, which are one of the main causes for fibrosis and adhesion formation, in anatomical areas which are located beside or close to the dura mater or spinal nerves.

In one example of the present invention the cells whose adhesion to the spinal nerves and/or the dura mater is prevented by the method according to the present invention are selected from connective tissue cells. The mammal may be any mammal, such as humans, mice, rats, cats, dogs, etc.

Figure 5A:
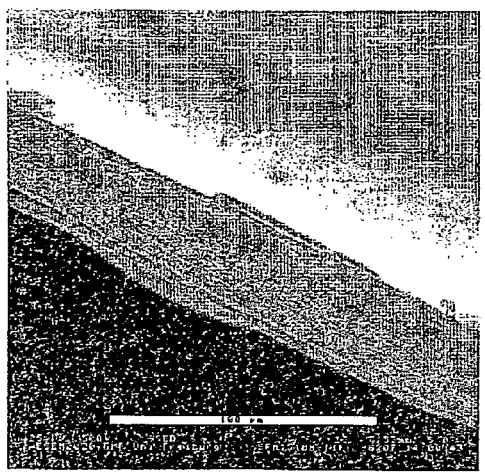
FIGS. 5A, 5B, and 5C are photographs taken under ESEM conditions (humid atmosphere) illustrating the cross section of a biofunctional collagen foil biomatrix. The material reveals a structure like a stack of sheets packed very tightly together. Interstices between the collagen layers are shown in the picture.
Figure 5B:
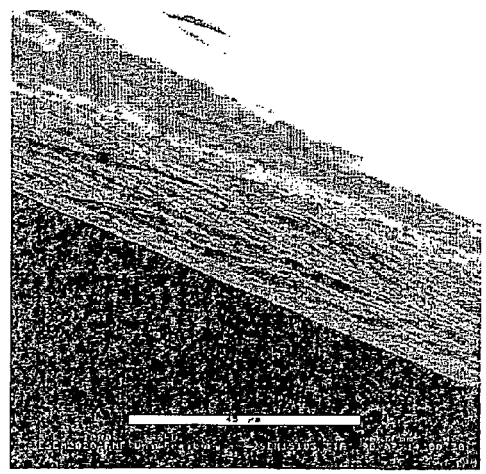
Figure 5C:
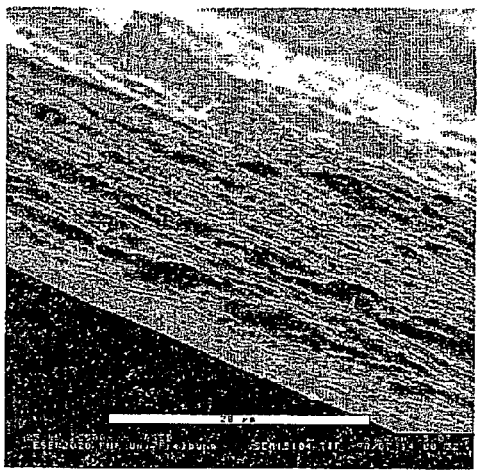
Figure 6A:
FIGS. 6A and 6B are SEM photographs illustrating the cross section of a dry biofunctional collagen foil biomatrix. Multiple layers of collagen and interstices between the collagen layers are illustrated in the pictures.
Figure 6B:

The step of covering and separating the tissue with a multilayered biofunctional collagen foil biomatrix may be carried out during the treatment of any injuries or defects of the spinal dura mater or the spinal column. In one example of the present invention, the step of covering and separating the tissue with a multilayered collagen foil biomatrix may be carried out during spinal surgery. In another example, the multilayered collagen foil biomatrix attracts cells such as repair cells and regeneration cells and directs their in-growth through and on the foil biomatrix. The multilayered collagen foil biomatrix is reabsorbed and remodeled to natural tissue by the in-growth of cells. The collagen foil biomatrix acts as a bioactive and biofunctional scaffold for cellular in-growth in vivo and is replaced by mammalian tissue during regeneration and restoration. The collagen foil biomatrix is resorbable by the mammal in which it is implanted. This property may be enhanced by the biofunctionality of the native cross-linked collagen fibers and the multilayered structure of the collagen foil biomatrix, as shown in FIGS. 5-6.

The process utilized to produce the collagen foil biomatrix used in the invention forms stacked layers of collagen fibrils. Between each layer are interstices into which cells and vasculature of the patient can migrate and form new collagen structures and native-conformation tissue. It is a beneficial property of the method according to the present invention that the biofunctional native collagen fibers and the non-porous, layered structure of the collagen foil biomatrix promotes the in-growth of cells, vasculature, and the formation of new collagen structures across the collagen foil biomatrix and in the interstices that exist between its multiple layers. As compared to random, unguided, non-controlled cellular in-growth at the wound or defect, the directed in-growth and regeneration in the methods of the invention prevents the formation of adhesions and fibrosis, maintaining the separation of the tissues in the spinal column anatomical structure. Thus, pain and complications associated with peridural or perineural adhesions and fibrosis are avoided.

Figure 7:
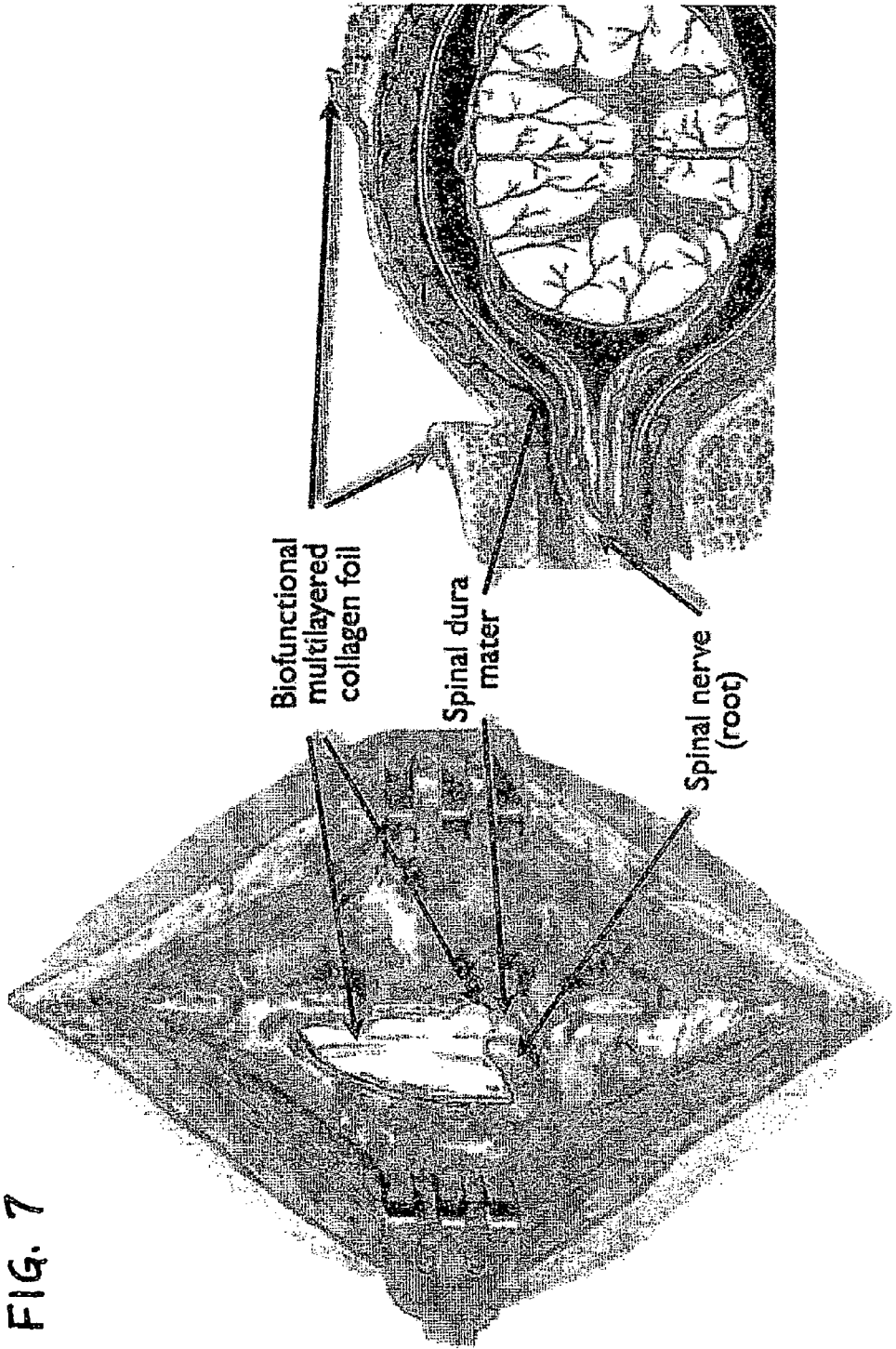
FIG. 7 is an illustration of one embodiment of the invention, in which the biofunctional collagen foil biomatrix is placed over the edges of a surgically produced defect in the vertebra, and on top of the dura mater, in order to direct cell in-growth and control tissue regeneration, thus preventing adhesion of the regenerating wound tissue to the spinal dura mater and spinal nerves. In this embodiment, the edges of the biofunctional collagen foil biomatrix are secured to the lateral exterior wound surface of the vertebra.
Figure 8:
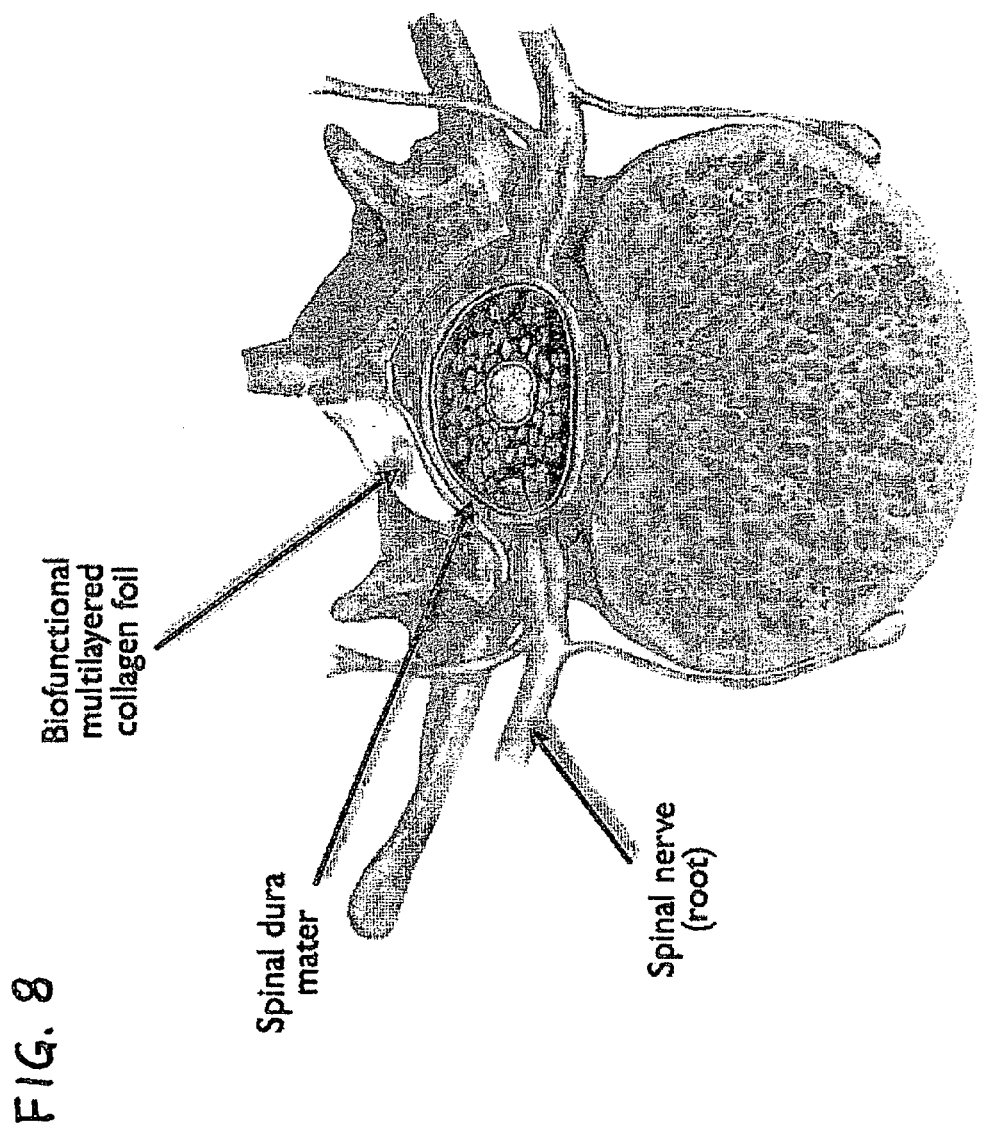
FIG. 8 is an illustration of another embodiment of the invention, in which the biofunctional collagen foil biomatrix is placed under a surgically produced defect in the vertebra, and on top of the dura mater, in order to prevent adhesion of the regenerating wound tissue to the spinal dura mater and spinal nerves. In this embodiment, the edges of the biofunctional collagen foil biomatrix are secured to the interior surface of the vertebra, in the spinal canal.

The phrase "covering the tissue with a multilayered collagen foil biomatrix" means, in general, bringing the tissue into physical contact with a multilayered collagen foil biomatrix. In one example of the present invention, the contacting of the tissue with a multilayered collagen foil biomatrix results in an implantation of said foil. Examples of the positioning of the multilayered collagen foil biomatrix are illustrated in FIGS. 7-8.

The phrase "multilayered collagen foil biomatrix" or "collagen biomatrix" or "collagen foil" as used herein means a biomatrix (i.e. a matrix of biocompatible and biofunctional material) of native collagen fibrils treated to remove non-collagenous components and to form a sheet of collagen fibrils with a multilayered laminar structure on a microscopic level. The multilayered collagen foil may be from any source, such as bovine, ovine, porcine, equine, or human origin treated to remove non-collagenous components and to form a sheet of collagen fibrils, with the same physical characteristics. The collagen foil biomatrix of the present invention is substantially non-porous, as determinable by scanning electron microscopy.

The term "biofunctional" as used herein in the context of a biofunctional multilayered foil biomatrix means that the biomatrix consists of native collagen fibrils that are recognized and utilized by the cells of an animal in a manner similar to the native collagen fibrils in the animal. For example, without limitation, such functions may include migration of repair and regeneration cells along the biofunctional collagen fibrils and the multi-layered structure, and the deposition of new extracellular matrix by the cells including, or replacing, the biofunctional collagen fibrils.

The phrase "non-naturally occurring biomatrix" as used herein means a manufactured matrix or framework comprising native collagen fibrils formed from (i) a material existing in nature (i.e. natural material) that has been treated or processed in a manner in which the collagen fibrils contained in the natural material have been moved or repositioned from their naturally-occurring arrangement within the collagen structure of the natural material; or (ii) a material not existing in nature (i.e. a non-natural, artificial material, such as a recombinant material) treated or processed to manipulate the arrangement of the collagen fibrils. For example, a non-naturally occurring biomatrix may be formed from starting material comprising collagen that has been mechanically or chemically processed (e.g. grounded, chopped, etc.). A collagen biomatrix that is formed from the treatment or processing of starting material in a manner that preserves the structure of the naturally occurring collagen framework is not a non-naturally occurring biomatrix (e.g. epidermal tissue treated to remove cellular components while preserving the naturally occurring collagen structure).

In one embodiment of the present invention, the collagen foil biomatrix is comprised of connective tissue proteins consisting of collagen fibrils. For example, the collagen foil biomatrix may be comprised of connective tissue proteins consisting of Type I collagen fibrils. In addition to being comprised of collagen fibrils, the collagen foil biomatrix can further comprise an excipient, a preservative, a growth factor, or an additive that aids in the flexibility and elasticity of the final product.

Each layer of collagen fibrils is substantially non-porous. The phrase "substantially non-porous" as used herein means that any pores that are present in a collagen foil biomatrix as a result of precipitation of collagen fibrils to form a collagen sheet are primarily isolated from one another. The pores are not interconnected in a manner that traverses the thickness of the collagen foil. Mechanical perforations that create holes in the collagen foil biomatrix are not pores. In one example of the present invention the material appears to be substantially free of pores that would be visible using a scanning electron microscope at 1500× magnification. Scanning electron microscope pictures illustrate the non-porous nature of the collagen foil biomatrix as in FIGS. 1-4.

Figure 1:
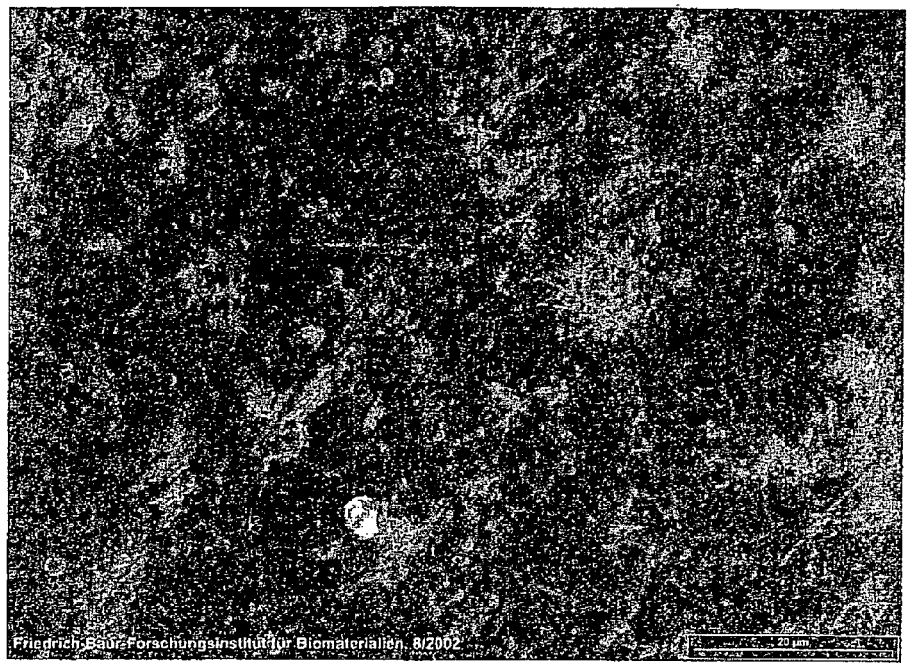
FIG. 1 is a SEM (scanning electron microscope) photograph illustrating the surface of a biofunctional collagen foil biomatrix. Collagen fibrils are clearly illustrated. Substantial non-porosity of the surface is evident from the picture.
Figure 2A:
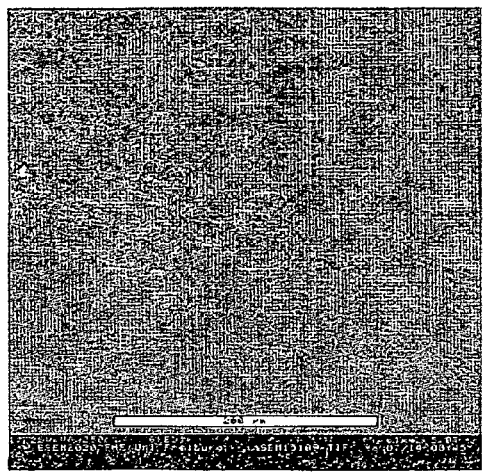
FIGS. 2A and 2B are photographs taken under ESEM (environmental scanning electron microscopy) conditions, which means near natural conditions in a slightly humid atmosphere, illustrating the upper surface, seen from the side of a biofunctional collagen foil biomatrix. Substantial non-porosity is evident from the photographs.
Figure 2B:
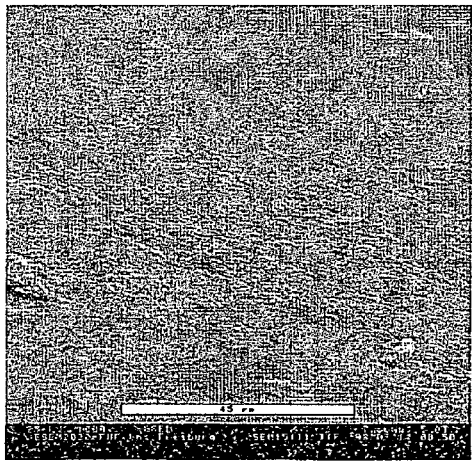
Figure 3A:
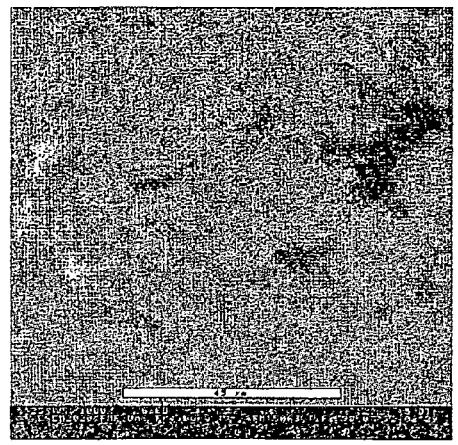
FIGS. 3A and 3B are photographs taken under ESEM conditions illustrating the lower surface of a biofunctional collagen foil biomatrix. Collagen fibrils are illustrated in FIG. 3A. Substantial non-porosity of the surface is evident from the pictures.
Figure 3B:
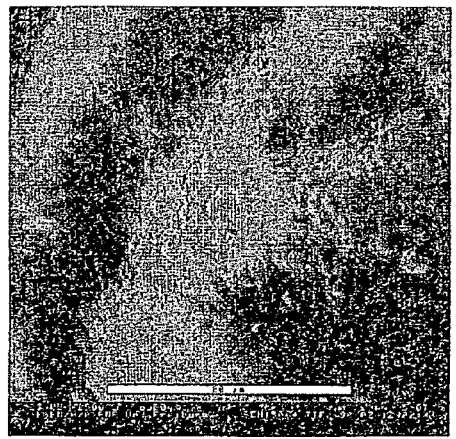
Figure 4:
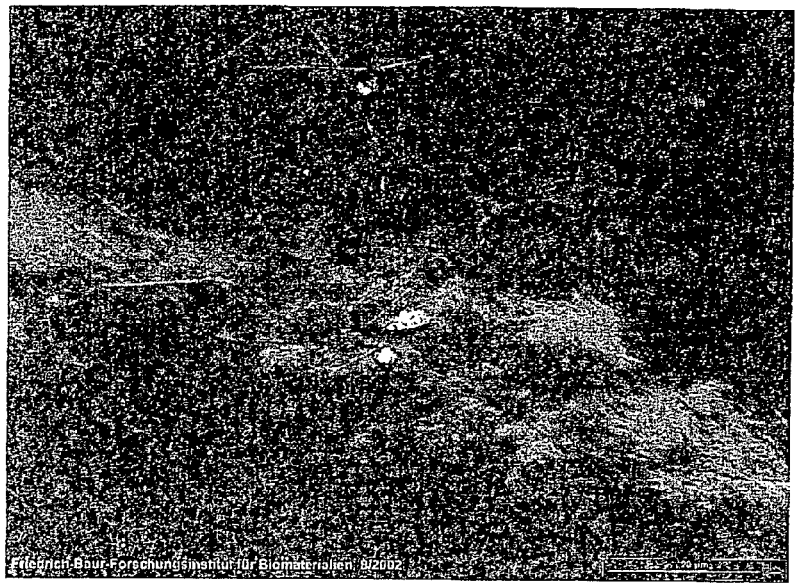
FIG. 4 is a SEM photograph illustrating the surface of a hydrated biofunctional collagen foil biomatrix. Collagen fibrils are clearly illustrated in FIG. 4. Substantial non-porosity of the surface is evident from the picture.

In one embodiment of the present invention, the collagen foil biomatrix utilized in the present invention is a non-naturally occurring multi-layered collagen membrane consisting of layers of numerous multi-directional intertwined collagen fibrils. Thus, the collagen fibrils are arranged in a multi-directional fashion in a plane, and these planes form sheets, which create a multi-layered structure. An illustration of a dry collagen foil biomatrix may be seen in a photomicrograph (SEM), which illustrates the surface of the collagen foil biomatrix in which collagen fibrils are embedded (FIG. 1). The collagen fibrils are visible on the surface on photographs of the upper surface of the collagen foil biomatrix under ESEM (Environmental Scanning Electron Microscopy) conditions, in which a slightly humid atmosphere provides near natural conditions. The surface appears smooth and substantially non-porous (FIG. 2). Photographs (ESEM) of the lower surface of collagen foil biomatrix illustrate the substantial non-porosity of the collagen foil biomatrix in FIG. 3.

The unique orientation of the collagen fibers in two-dimensional directions in the multiple layers is primarily responsible for a liquid-tightness, even under high hydrostatic pressure, and provides great strength with high elasticity. Due to the numerous parallel-oriented thin collagen fibril layers of the collagen foil biomatrix, this material is suitable for temporarily replacing the body's own tissue in closing and separating the defect after covering and provides a biofunctional biomatrix scaffold for cell in-growth for forming a new tissue. The multiple layer structure of the present invention enhances the liquid-tight characteristic of the collagen foil biomatrix.

While the collagen foil biomatrix is substantially non-porous, interstices exist between the layers of collagen fibrils. The collagen foil biomatrix is analogous to a stack of pages wherein each page is substantially smooth and non-porous, with a space between each page. When in its dry form the interstices are more pronounced. The interstices become reduced when the collagen foil biomatrix is observed under near natural conditions in a slightly humid atmosphere. The reduction of the interstices of the collagen foil biomatrix is illustrated in pictures of cross sections of collagen foil biomatrix in a humid atmosphere in FIG. 5. In addition to promoting a liquid-tight property, the numerous parallel-oriented thin collagen fibril layers of the collagen foil biomatrix simultaneously serve as a bioequivalent biofunctional scaffold for cell in-growth for de novo construction of the body's own tissue.

The change in volume of the collagen foil biomatrix used according to the present invention is small or negligible when hydrated. In contrast to porous replacement products, the collagen foil biomatrix substantially retains its size and shape upon being hydrated, having excellent shape stability even after hydration, and causing no problems of swelling or shrinking following the contact with the tissue. Once hydrated and implanted, collagen foil biomatrix does not significantly expand or contract in area or thickness to the extent that it would tear surgical sutures or break apart fibrin or other biocompatible glue seals that hold the collagen foil biomatrix to the patient's tissue.

In one example of the present invention, the shrinking or swelling of the area of the dry collagen foil biomatrix may vary from about −5% to about 20% when completely hydrated. In another example, the area of the dry collagen foil biomatrix may vary between about −5% to about 10% when completely hydrated. In a further example, the area of the dry collagen foil biomatrix varies between about −5% to about 5% when completely hydrated. For example, the area of the dry collagen foil biomatrix increases no more than about 4 percent when completely hydrated.

In one example of the present invention, the collagen foil biomatrix increases up to about 6 times its dry thickness when it is completely hydrated. In another example, the collagen foil biomatrix increases up to about 3 times its dry thickness when it is completely hydrated. In another example, the collagen foil biomatrix increases to about twice its dry thickness when it is completely hydrated.

The thickness of the collagen foil biomatrix for use in the present invention may vary as required by a particular application. Varying the amount of starting material utilized to produce a particular size of collagen foil biomatrix can control the thickness of the collagen foil biomatrix. In one example of the present invention, the collagen foil biomatrix used according to the present invention, when in its dry form, has a thickness between about 0.01 mm to about 3.0 mm. In another example, the collagen foil biomatrix has a thickness between about 0.02 mm to about 2.0 mm. In a further example, the collagen foil biomatrix has a thickness between about 0.03 mm to about 1.5 mm. In another example, the collagen foil biomatrix has a thickness between about 0.05 mm to about 1 mm. In still another example, the collagen foil biomatrix has a thickness of about 1.0 mm or less.

The dry weight of the collagen foil biomatrix is dependent on its desired thickness. In one example, the dry weight of the collagen foil biomatrix is between about 1 mg/cm$^2$ to about 50 mg/cm$^2$. In another example, the dry weight of the collagen foil biomatrix is between about 1.5 mg/cm$^2$ to about 30 mg/cm$^2$. In still another example, the dry weight of the collagen foil biomatrix is between about 2 mg/cm$^2$ to about 20 mg/cm$^2$. In a further example, the dry weight of the collagen foil biomatrix is between about 2.5 mg/cm$^2$ to about 15 mg/cm$^2$. For example, the dry weight of the collagen foil biomatrix is between about 3 mg/cm$^2$ to about 10 mg/cm$^2$.

In one example of the present invention, the weight of the collagen foil biomatrix increases up to about 15 times its dry weight upon hydration. In another example, the weight of the collagen foil biomatrix increases up to about 10 times its dry weight upon hydration. In another example, the weight of the collagen foil biomatrix increases up to about 7 times its dry weight upon hydration. In still another example, the weight of the collagen foil biomatrix increases up to about 5 times upon hydration from its dry state.

The collagen foil biomatrix used according to the present invention beneficially has high tensile strength, which improves and supports the handling of the collagen foil biomatrix e.g. during its surgical application and provides an increased mechanical stability, e.g., after its implantation. Additionally, increasing the thickness of the collagen foil biomatrix can significantly increase the tensile strength.

The propensity of collagen foil biomatrix material to tear under exerted pressure may be measured as its "ultimate tensile load" or "ultimate tensile force," hereinafter referred to as "ultimate tensile force." The ultimate tensile force of a collagen foil biomatrix may be determined by subjecting pressure to a strip of collagen foil biomatrix having a specified width and determining the amount of pressure applied that results in failure (e.g., tearing or rupturing) of the collagen foil biomatrix. Ultimate tensile force may be quantified using the following equation: "Ultimate Tensile Force"=force applied/width of collagen foil biomatrix strip=Newtons/cm-strip.

In one example of the present invention, the collagen foil biomatrix has an ultimate tensile force between about 1 and about 30 Newtons/cm-strip, for example between about 1.5 and about 15 Newtons/cm-strip, for example between about 2 and about 10 Newtons/cm-strip, for example between about 3 and about 6 Newtons/cm-strip.

While the collagen foil biomatrix used according to the present invention has a high tensile strength, it remains elastic and flexible when hydrated. This feature permits the collagen foil biomatrix to optimally adapt to the anatomic conditions (e.g. curves) present at the contact site.

When in its hydrated state, the collagen foil biomatrix can be easily moved around e.g. in the surgical site and optimally modeled and adapted to the shape and position of the defect e.g. where it is being implanted. Once implanted, the collagen foil biomatrix graft remains smooth and may be repositioned if necessary. Over time, cells and vasculature migrate directed throughout the multiple layers of the multilayered collagen foil biomatrix, eventually replacing the multilayered collagen foil biomatrix with a new tissue. As cells migrate and vasculature forms within the layers of the collagen foil biomatrix, the tissue takes on the form of the collagen foil biomatrix in a directed way. After cellular organization of the collagen foil biomatrix with the newly formed connective tissue, adhesion formation to the spinal dura or spinal nerve tissues is minimized.

Collagen for use in manufacturing the collagen foil biomatrix may be obtained from any suitable source. For example, without limitation, collagen may be of bovine, ovine, porcine, equine, or human origin. The collagen may be harvested from a naturally occurring tissue, such as tendon, corium, or other collagen rich tissue or may be produced by recombinant genetic means. As described below, one exemplary embodiment of the invention utilizes equine collagen derived from Achilles tendon.

During the manufacturing process, e.g. as described in WO 04/108179, the collagen fibrils become naturally cross-linked as the fibrils precipitate out of solution to form a collagen foil. Unlike cross-linking the collagen fibrils with chemicals or radiation (e.g. ionizing or ultraviolet radiation), allowing natural cross-linking of the collagen fibrils ensures their bio-functionality, promotes accelerated regeneration, and reduced resorption times once the collagen foil biomatrix is brought into contact with the tissue. Cross-linking collagen fibrils with chemicals or radiation can result in increased resorption times, or even non-resorption, encapsulation, and scar formation. The natural cross-linking of the fibrils in the collagen foil biomatrix utilized in the invention occurs by natural, physiological-like means. Primarily this natural cross-linking is through non-covalent interactions (e.g. van der Waals or dipole-dipole interactions) or by the formation of readily dissociable Schiff-base bonds between the amino acid side chains of the collagen molecule. Intermolecular cross-linking of collagen is responsible for physical and chemical stability. The key step in the formation of collagen cross-links depends on the enzymatic conversion of lysine or hydroxylysine residues and gives rise to aldehydes, allysine and hydroxyallysine. These aldehyde groups spontaneously react with reactive amino groups resulting in the formation of Schiff-base components containing labile aldolcondensation products with labile aldimine links (like for example —CH=N—). Thus, the fibrils of the product of the present invention may be dissociated by treatment with, for example, a weak acid. Cross-linking arising from the use of chemical cross-linking agents can be detected from the presence of stable covalently cross-linked cross-linking moieties. Commonly, this is accomplished by using a Schiff-base reagent (e.g. glutaraldehyde) to form Schiff-base reaction products, and then stabilizing the bonds through either an Amadori-rearrangement or reducing conditions. In addition collagen can be cross-linked by various bifunctional carbodiimide reagents. Cross-linking arising from the use of radiation can be detected by the presence of stable covalent bonds between the collagen fibrils, caused by the reaction of free radical moieties generated during irradiation. The fibrils in the product of the present invention, on the other hand, are substantially uncross-linked with any stable covalent bonds, and have not been treated in a chemical or irradiative manner. Thus, any associations between the fibrils in the product of the invention are substantially non-covalent or readily reversible, and are not stably cross-linked. Chemicals such as cyanamide, glutaraldehyde, formaldehyde, acrylamide, carbodiimidediones, diimidates, bisacrylamides, and the like have been utilized in the past to chemically cross-link collagen fibrils. Use of such chemicals, however, may result in toxicity risks associated with inadvertently contacting neural tissue with residual chemicals in the collagen foil biomatrix. The precipitation process thereby avoids the toxicity risks of cross-linking chemicals and longer resorption times associated with cross-linking the collagen fibrils with chemicals or radiation.

The resulting dried, precipitated, collagen composition forms an collagen foil biomatrix comprised of a high-molecular weight multi-layered collagen membrane consisting of numerous layers of two-dimensionally multi-directional naturally intertwined collagen fibrils. The collagen foil biomatrix primarily contains interstitial Type I collagen. The collagen foil biomatrix has substantially no pores and is primarily liquid-tight. Immune diffusion tests may be conducted on the product to guarantee the absence of foreign protein. The collagen foil biomatrix may be gas-sterilized with ethylene oxide (ETO) or similar sterilization gas or by irradiation.

A significant benefit of using an equine collagen foil biomatrix according to the present invention is the substantially low risk of transmitting a disease to a patient being contacted with said foil. The manufacturing process in which the collagen fibrils are treated with acids (e.g. hydrochloric acid, acetic acid, and the like) and bases, such as sodium hydroxide, to produce the equine collagen foil beneficially acts to inactivate or reduce the infectious levels of bacteria, viruses, and prions that may be present. Treatment of biomaterial with hydrochloric acid, sodium hydroxide, ethylene oxide (ETO), and the like have been recognized in the prior art as approved methods within drug and biomaterial regulations to inactivate prions and viruses. Such treatment may, under some regulations, reduce the regulatory requirements for testing the equine collagen foil on a batch-by-batch basis. Thus, the treatment of the collagen fibrils during the manufacturing process enhances the product safety and reduces the risk of disease transmission to a patient.

Equine material that has been subjected to the manufacturing process described above is not known to transmit any pathogens to patients. Thus, in addition to the manufacturing process, utilization of equine-based collagen further avoids the risks of transmitting spongiform encephalitis that have been previously associated with human cadaveric materials.

The use of collagen derived from an equine origin, such as collagen derived from equine Achilles tendons avoids the risks of transmitting transmissible spongiform encephalopathy (TSE), which is also known as bovine spongiform encephalopathy (BSE) or scrapie. Transmission of this disease has been associated with the use of biological material obtained from ruminant sources (e.g. biological material from cattle, goats, sheep, and the like).

The collagen foil biomatrix used according to the present invention, wherein the collagen is derived from an equine origin and treated (e.g. with enzymes) additionally reduces the risk of eliciting an immune response.

Equine-derived collagen foil biomatrix also results in a reduced inflammatory response. When compared to foils that contain collagen derived from sources such as human fascia lata, the number of inflammatory cells resulting from the contact with the equine collagen foil biomatrix is significantly lower.

Prior to use, the dry collagen foil biomatrix may be hydrated, e.g. in physiological saline. In one example, the physiological saline comprises a 0.9% sodium chloride solution. In another example, the collagen foil biomatrix is hydrated in excipients or drug-containing solutions. The length of time necessary to hydrate the collagen foil biomatrix is related to the thickness of the foil. The collagen foil biomatrix is hydrated until it is consistent in thickness across its entire area. In one example the collagen foil biomatrix is hydrated between about 0.5 seconds and about 1 hour in physiological saline. In another example the collagen foil biomatrix is hydrated between about 0.5 seconds and about 30 minutes in physiological saline. In another example the collagen foil biomatrix is hydrated between about 0.5 seconds and about 20 minutes in physiological saline. In another example the collagen foil biomatrix is hydrated between about 0.5 seconds and about 10 minutes in physiological saline. In still another example the collagen foil biomatrix is hydrated between about 0.5 seconds and about 2 minutes in physiological saline. In another example the collagen foil biomatrix is hydrated about 0.5 seconds to ten seconds in physiological saline, e.g., by dipping the collagen foil biomatrix into physiological saline. In another example the collagen foil biomatrix is not hydrated prior to contacting the tissue.

The collagen foil biomatrix may be attached to the patient's tissue by established surgical techniques, e.g. by fibrin sealant, tissue glue, surgical sutures, or by pressure fitting surgical techniques. Alternatively, the natural attraction between the collagen foil biomatrix and the tissue, or the blood on the surface of the tissue, can be used to attach the collagen foil biomatrix to the tissue without the use of any sealant, glue, sutures, or pressure fitting techniques. Once hydrated, the collagen foil biomatrix can be cut slightly larger than e.g. the surgical opening in the patient's tissue. The collagen foil biomatrix thereby slightly overlaps the patient's tissue to which it is attached. In one example, the hydrated collagen foil biomatrix is sized to have an approximately 0.5 cm to about 1 cm overlap with the tissue. The amount of overlap can vary depending on the preferences and skill of the surgeon.

In one example, according to the well-known interaction of collagen with fibrinogen and fibronectin, the collagen foil biomatrix can be fixed in place with fibrin sealant. Examples of fibrin sealant approved for surgical use include TISSUCOL and TISSEEL fibrin sealants (Baxter AG, Vienna, Austria). Alternatively, a tissue glue that does not induce an extensive inflammatory reaction, and is approved for use in spinal surgery, may also be utilized. The fibrin sealant or tissue glue may be applied in a continuous line around the portion of the collagen foil biomatrix that overlaps the tissue in order to form a liquid-tight seal. A liquid-tight seal fixation is advantageous as it avoids complications associated with contact of the adjacent tissues with hemorrhages, e.g., induction of adhesion formation by fibrin. In another example the collagen foil biomatrix produces a liquid-tight seal when attached to the tissue with a continuous line of fibrin sealant or tissue glue. In a further example the collagen foil biomatrix that overlaps the tissue can be dotted with fibrin sealant or tissue glue to attach it to the tissue. In still another example the collagen foil biomatrix is attached by surgically suturing it to the tissue once it has been positioned to the desired contact site. If the collagen foil biomatrix is to be sutured, tensionless suturing techniques must be used to prevent tearing the foil. It is recommended to seal suture lines, for example, with a fibrin sealant. In another example, the collagen foil biomatrix is positioned and implanted according to pressure fitting techniques known in the art. In this technique, the collagen foil biomatrix is positioned in the desired implantation site and held in place by the surrounding tissues. Thus, the graft remains in place without the use of surgical sutures, fibrin sealant, or tissue glue. In another example, the collagen foil biomatrix is positioned and implanted without the use of any sealant, glue, sutures, or pressure fitting techniques. In this technique, the collagen foil biomatrix is positioned in the desired implantation site and held in place by the natural attraction or adhesion that occurs between the collagen foil biomatrix and the mammalian tissue. In another example, the collagen foil biomatrix may be applied to a tissue and affixed by any of the methods above, and then another collagen foil biomatrix may be applied to an adjacent tissue, and applied by any of the methods above, thus resulting in adjacent sheets of the collagen foil biomatrix.

Optionally, the collagen foil biomatrix of the present invention may be utilized in conjunction with other products. For instance, after applying the collagen foil biomatrix to the tissue and securing by any of the means described above, an ant-adhesion product may be applied to the upper or lower surface of the collagen foil biomatrix, or to adjacent tissues. In one embodiment, a PEG based product, such as CoSeal® (available from Baxter Healthcare corporation) may be applied to the upper or lower surface of the collagen foil biomatrix, or to adjacent tissues. As the collagen foil biomatrix of the invention prevents adhesion by separating tissues and by directing tissue regeneration, rather than by creating a "slippery" surface, its action may be complemented by utilizing products that temporarily create a "slippery" surface to which cells will not adhere. In another embodiment a ready-to-use collagen foil biomatrix, which is already coated with a PEG-based product on one or both surfaces may be used.

Additionally, the present invention is related to the use of a multilayered collagen foil biomatrix in the manufacture of a medicament, i.e. a medically applicable material, for treating a disorder such as e.g. injuries, surgeries, or pathogen-based diseases, in a mammal characterized by a disconnection of a tissue selected from the group consisting of spinal column and dura mater, and the surrounding tissue.

EXAMPLES

Adhesion and Fibrosis Formation, Basics and Study Goal

Excessive scar tissue formation and adhesion is a serious problem in spine surgery, frequently causing radicular pain and physical impairment, e.g., failed lumbar disc surgery or post discectomy syndrome. The incidence of dura mater lesion in case of revision surgery is reported between 5 and 10% in the literature.

The most important critical parameters for the postoperative development and extent of adhesion formation are:
- the preoperative situation of the surgical area (existing adhesions/fibrosis, inclusive a genetically predisposition of the patient);
- the intraoperative performance of the surgery (extent of wound area, avoidance of injuries of tissues and certain anatomical structures (e.g. membranes), carefulness of hemostasis, avoidance of drying out of tissues etc.); and,
- intraoperative measures for prevention and minimization of postoperative adhesions, e.g. implantation of anti-adhesive implants like sponges, foils or gel.

Due to the multiple causes of adhesions, surgical measures may never reach a 100% adhesion prevention in every patient but preconditions of the above mentioned parameters can be influenced. The surgical goal is the optimization of the surgical wound situation during and in the early postoperative period. It is known that wound conditions in this period are mainly responsible for the formation of any postoperative adhesion and fibrosis formation.

Considering the pathogenesis of adhesions/peridural fibrosis, the investigation of the behavior of potentially dura protecting and adhesion preventing and minimizing methods and products during the physiological scar formation in the peridural dorsal wound area is focused on the first postoperative period (approx. one to two weeks post surgery). This is the most important time period to determine whether a particular composition fulfills the function of protecting and separating the dura mater from the scar formation in the dorsal surgical defect area and the avoidance of uncontrolled postoperative distribution of blood, fibrinogen, fibrin and necrotic material, which are the main factors and underlying cause for any uncontrolled scar/adhesion/fibrosis formation.

The situation at two weeks post-operation allows the evaluation of the integration of the implant and conclusions of the kind and potential of the bioactivity, biofunctionality and tissue compatibility of implants. For example, after two weeks, is the implant well accepted, cellularized and integrated into the dorsal anatomy or, in contrast, does it act as a long term foreign body and provokes encapsulations and scar formation? The aim of the following Examples is to evaluate the biofunctionality as a temporary separation layer and as biomatrix for cell growth and tissue regeneration of a biological collagen foil biomatrix in the postoperative period and the value for the prevention and minimization of clinically relevant adhesion and uncontrolled scar tissue formation.

Example I

Figure 9:
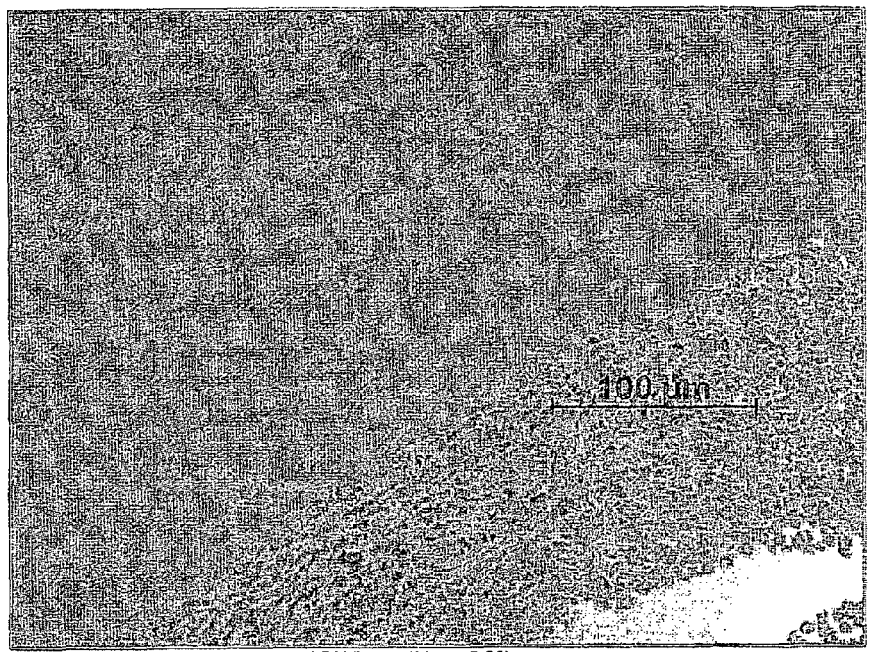
FIG. 9 is a sectional view of the collagen foil biomatrix one week postoperatively. The structure of the surface is non-porous and forms a temporary barrier. Blood (erythrocytes) are separated and did not penetrate into the multi-layered collagen foil biomatrix.

Materials and Methods: Animal Experiments Showing Reduced Adhesions in Spinal Surgery Using the Biofunctional Collagen Foil Biomatrix A) Materials and Methods as shown in FIGS. 7-9:
Animals: New Zealand White rabbit, both genders, weight 4 kg. Origin: Charles River, Sulzfeld, Deutschland or Harlan Winkelmann, D-33178 Borchen.
Models and Groups:
Use of a biofunctional collagen foil biomatrix: Laminectomy, exposure of the spinal nerve root and application of the collagen foil biomatrix. Each group includes 20 animals.
Group 1: Laminectomy, Skin closure (Control).
Group 2: Laminectomy, Covering with collagen foil biomatrix.

Surgery:
The animals were positioned in a prone position and secured with the surgical area (lumbar spine) shaved. Under sterile conditions, after median incision of the skin, the Para vertebral musculature was detached from the spinous processes and the laminae of the lumbar vertebral spinal column exposed. Hemilaminectomy of the $3^{rd}$ and $4^{th}$ lumbar vertebra was conducted. Exposure of the two corresponding spinal nerve roots and of the root channels. Continuation of surgery in accordance with the different groups is also described.
General anaesthesia: Ketavet 60 mg/kg
Rompun 16 mg/kg s.c.
Thiopental i.v. through ear vein, based on effect
Narkosis, intubation, mechanical ventilation
Pain medication: 2× day. Temgesic 0.05 mg/kg s.c. for 3-4 days post operative.
Euthanasia: In general anesthesia barbiturate overdose i.v.
Evaluation and pathological examination:
Each group of animals were euthanized as follows: 10 animals after 10 days, 10 animals after 4 weeks and 10 animals after 3 months. Evaluation parameters: Extent of adhesions and fibrosis. Subsequently, an extensive histology was worked up. Experiments showed reduced adhesion formation in the group utilizing the biofunctional collagen foil biomatrix.

Example II

Collagen Foil Biomatrix One Week After Implantation in Human Patient

The human patient (age: 18, gender: female) was operated in the interval of 7 days in the frame of a routine surgical treatment (epilepsy). The collagen foil biomatrix was implanted epidural during the first surgery (prevention of CSF leaks). During the second surgery, the collagen foil biomatrix implant was removed routinely before the reopening of the dura. After one week of epidural implantation, the collagen foil biomatrix is still mechanically stable and removable as shown in FIG. 10.

Figure 10:
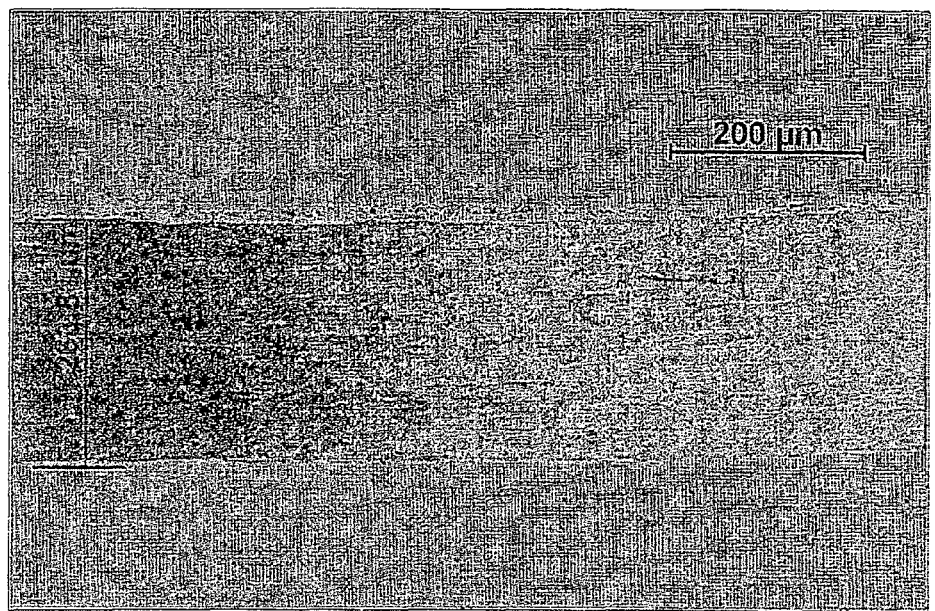
FIG. 10 shows the collagen foil biomatrix one week after implantation. The human patient (age: 18, gender: female) was operated in the interval of 7 days in the frame of a routine surgical treatment (epilepsy). The collagen foil biomatrix was implanted epidural during the first surgery (prevention of CSF leaks). During the second surgery the collagen foil biomatrix implant was removed routinely before the reopening of the dura. After one week of epidural implantation the collagen foil biomatrix is still mechanically stable and removable.
Figure 11:
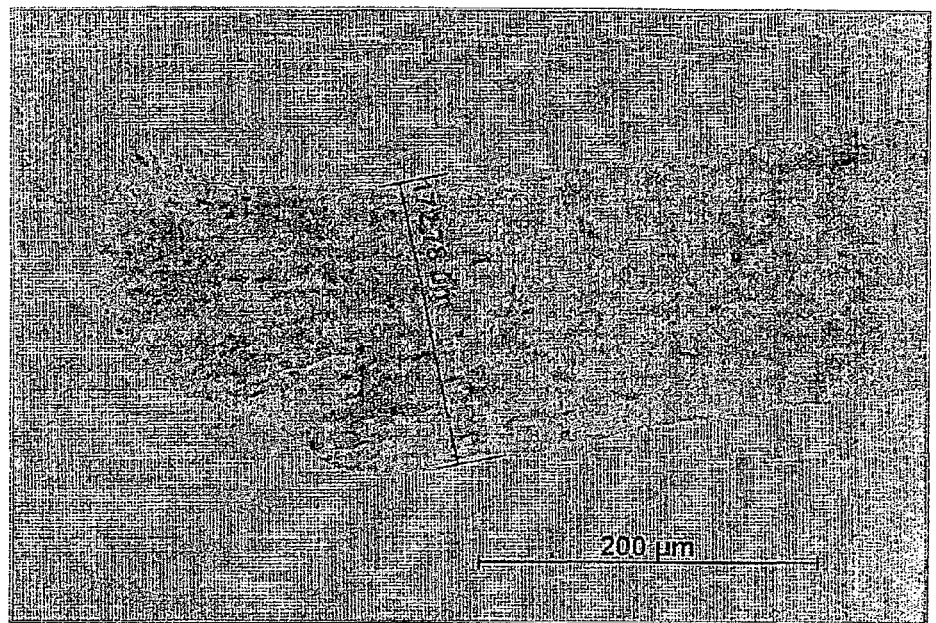
FIG. 11 is a sectional view of the collagen foil biomatrix rim one week after implantation. Fibroblasts have invaded the biomatrix to about 25 µm from the lower side and are spreading in a directed longitudinal in-growth along the parallel multi-layered structures and are growing into the collagen foil biomatrix, directed by the multi-layer structure. The penetration in longitudinal direction is about 220 to 320 µm. The speed of the directed in-growth of repair cells along the multi-layered structure is about 10 to 15 times higher in longitudinal direction compared to the transversal direction ("FIG. 10"). Minimal inflammatory infiltration, expressing the ongoing regenerative process.

FIG. 11 is a sectional view of the collagen foil biomatrix of FIG. 10 one week after implantation. As can be seen, fibroblasts are growing into the collagen foil biomatrix, directed by the multi-layer structure. The penetration in longitudinal direction is about 220 to 320 µm.

The speed of the directed in-growth of repair cells along the multi-layered structure is about 10 to 15 times higher in longitudinal direction compared to the transversal direction ("FIG. 10"). Minimal inflammatory infiltration is shown, expressing the ongoing regenerative process.

Example III

Cell Growth, Tissue Regeneration and Prevention of Peridural Adhesion and Fibrosis After Implantation of a Collagen Foil Biomatrix in Spinal Surgery Materials:
Native equine collagen fibrils (mainly type I collagen) produced from purified minced Achilles tendon from horses and precipitated to fibrils. The flexible formstable and elastic biomatrix is specially engineered and has a nonporous fluid tight multilayer structure. The thickness of the dry equine multilayered collagen foil membrane was about 0.1 mm. In the wet condition the membrane thickness growth up to 0.3 mm.

General anaesthesia: Ketavet 60 mg/kg
Rompun 16 mg/kg s.c.
Thiopental i.v. through ear vein, based on effect
Narkosis, intubation, mechanical ventilation
Pain medication: 2× day. Temgesic 0.05 mg/kg s.c. for 3-4 days post operative.
Euthanasia: In general anesthesia barbiturate overdose i.v.
Animal Model:

The present study was performed on New Zealand White ("NZW") rabbits weighing on average 3 kg at the time of surgery and their average age was 4 months. All rabbits were female and approval for the animal studies were performed after formal approval by the authorities of the city of Vienna, Austria. The design of surgery in this experimental animal model in rabbits was similar to the most common operative intervention in humans. A laminectomy and resection was performed of the facet joint at the lumbar spine 4 to 5 (L4/5). To carry out the full extend of a real surgery such as a Posterior Lumbar Interbody Fusion (PLIF) surgery, the ligamentum flavum was resected. The dura above the spinal cord remained intact. The laminectomy area was covered by a biological collagen foil biomatrix of the present invention. The paravertebral muscle was moved back in place and the fascia was closed by absorbable sutures. The skin was closed using syntofil sutures.

The rabbits received postoperative pain medication and fluid infusion during the first three days and received mixed food. The rabbits were euthanized by overdose of thiopental and the operated areas of the spine were removed and isolated for histological evaluation.

Histological Methods:

The vertebral column was excised en bloc and immersed in 10% formalin solution for fixation. After decalcification each lumbar vertebra was cut into slices, dehydrated and embedded in paraffin. Seven sections 3 μm thick were taken from each sample.

The sections were stained with Haematoxilin-Eosin for general histology staining all cells and bone components The slides were examined by evaluating anatomical structures like relation between dura mater and the peridural dorsal surgical wound area, cell in-growth into the collagen foil biomatrix and the absence/presence and extent of adhesion formation and peridural fibrous scar formation.

Results/ Histological Findings:

The sections were stained with Haematoxilin-Eosin for general histology staining all cells and bone components The slides were examined by evaluating anatomical structures like relation between dura mater and the peridural dorsal surgical wound area. Cell growth into and on the collagen foil biomatrix and the quantity and quality of the inflammatory reaction in the biomatrix and surrounding tissue were analyzed. The integration/incorporation process and the absence/presence and extent of adhesion formation and peridural connective tissue organization were also analyzed.

Figure 12:
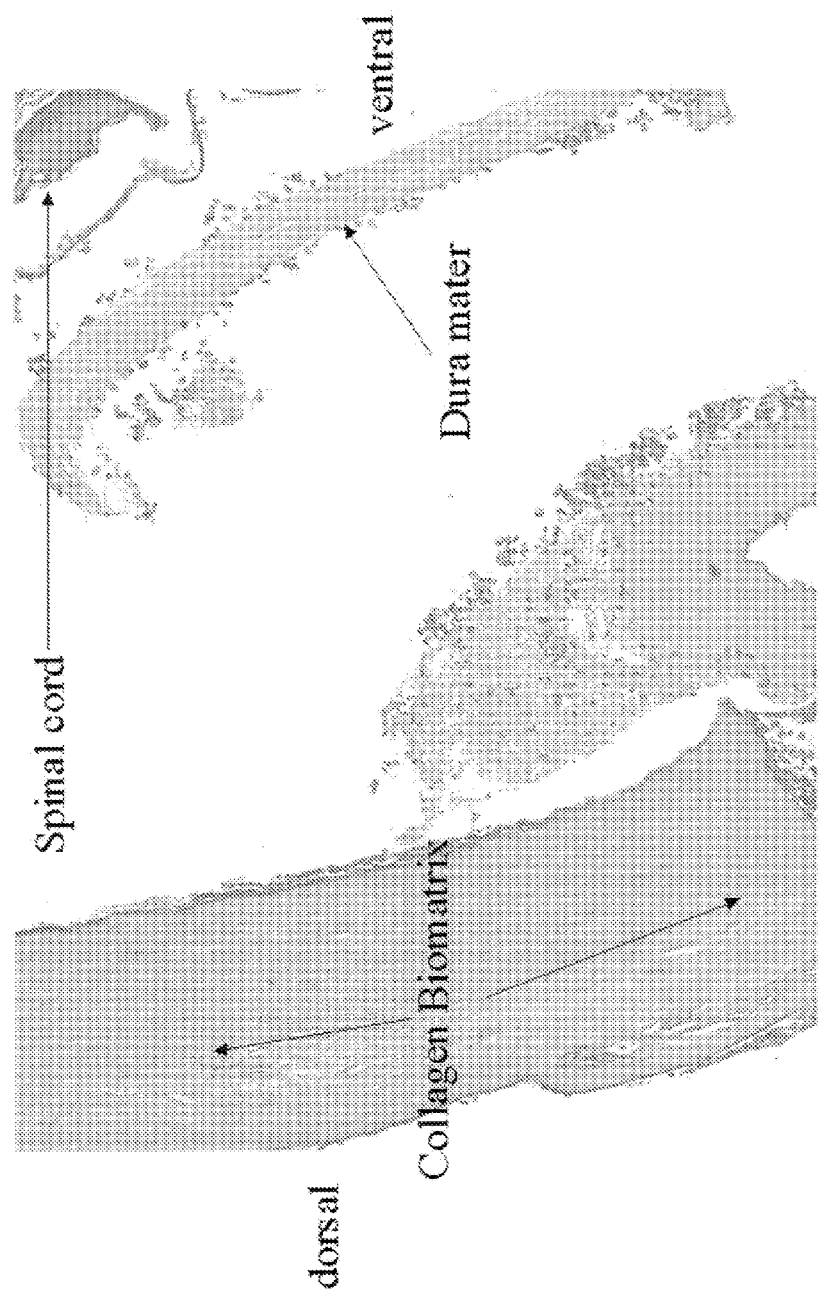
FIG. 12 shows postoperative slides of a New Zealand white ("NZW") rabbit with magnification ×20 with HE staining as taught in Example I. The multilayered collagen foil biomatrix is a separation layer between the dura mater and the dorsal wound area and provides a bioactive multilayer structure which is nonporous and fluid-tight to blood.
Figure 13A:
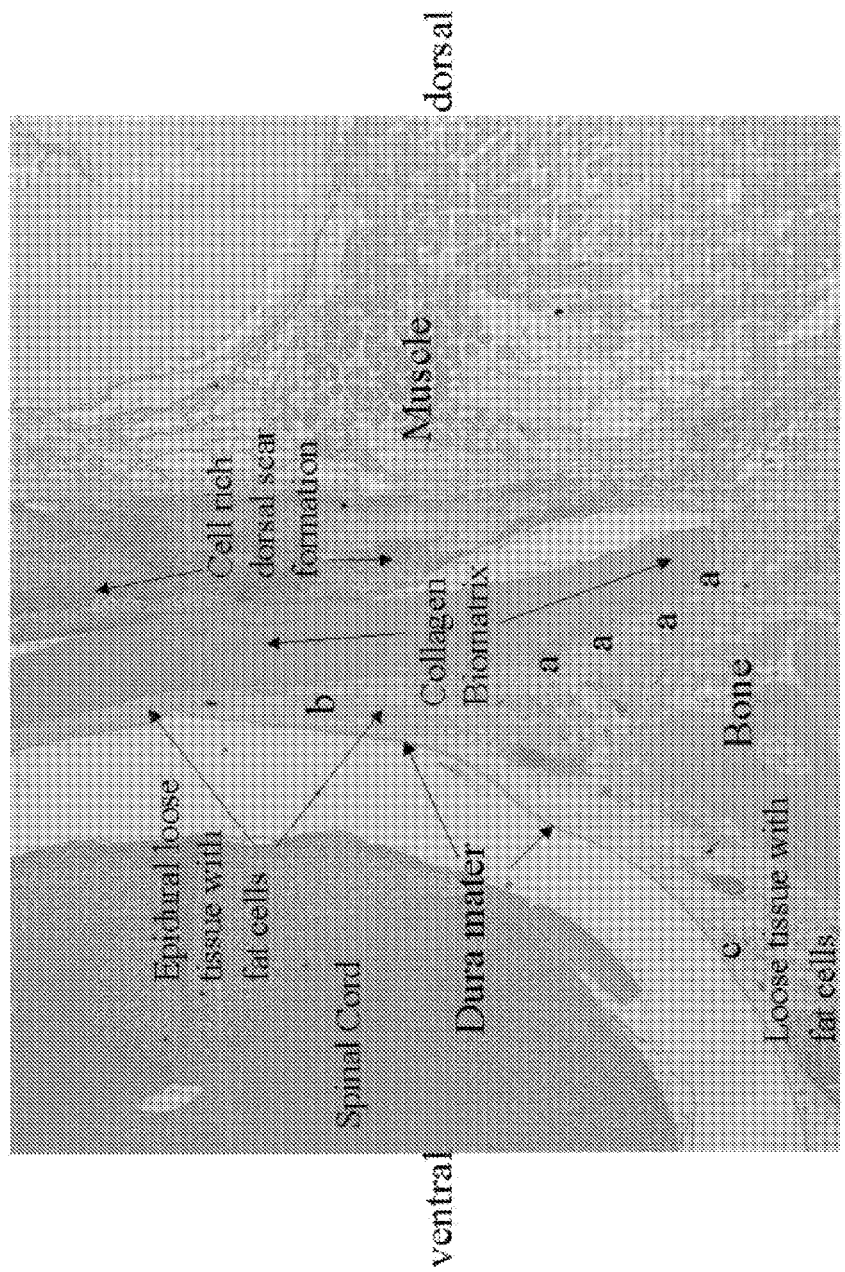
FIG. 13 A shows a NZW rabbit 1 week postoperative; Magnification: ×2.5; HE staining. The multilayered collagen foil biomatrix is closing the laminectomy defect and separating the epidural space from the beginning cell rich dorsal scar formation.
Figure 13B:
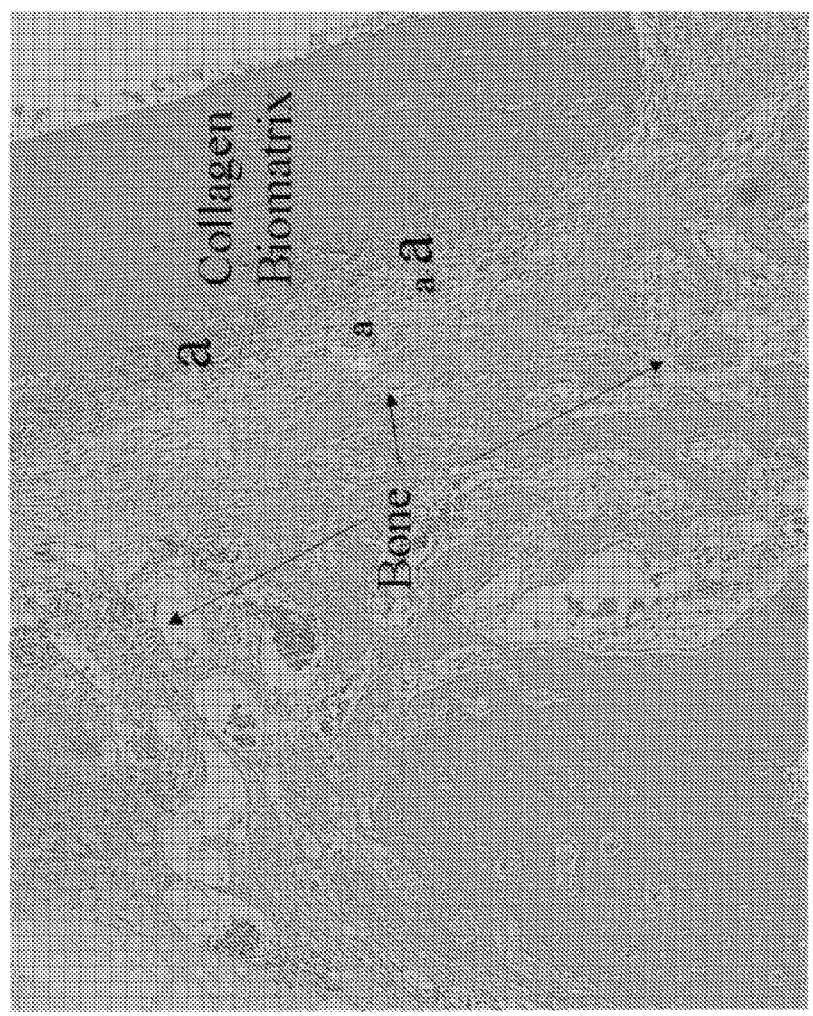
Figure 13C:
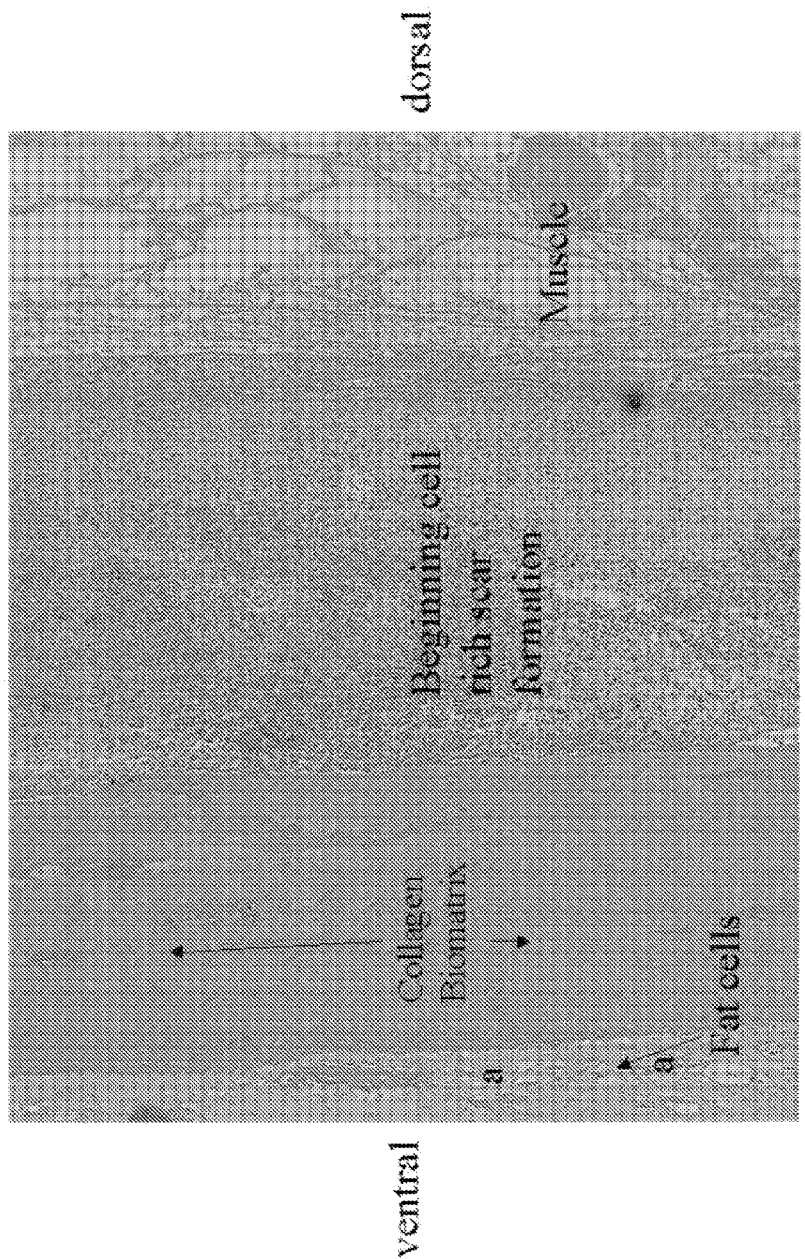
Figure 13D:
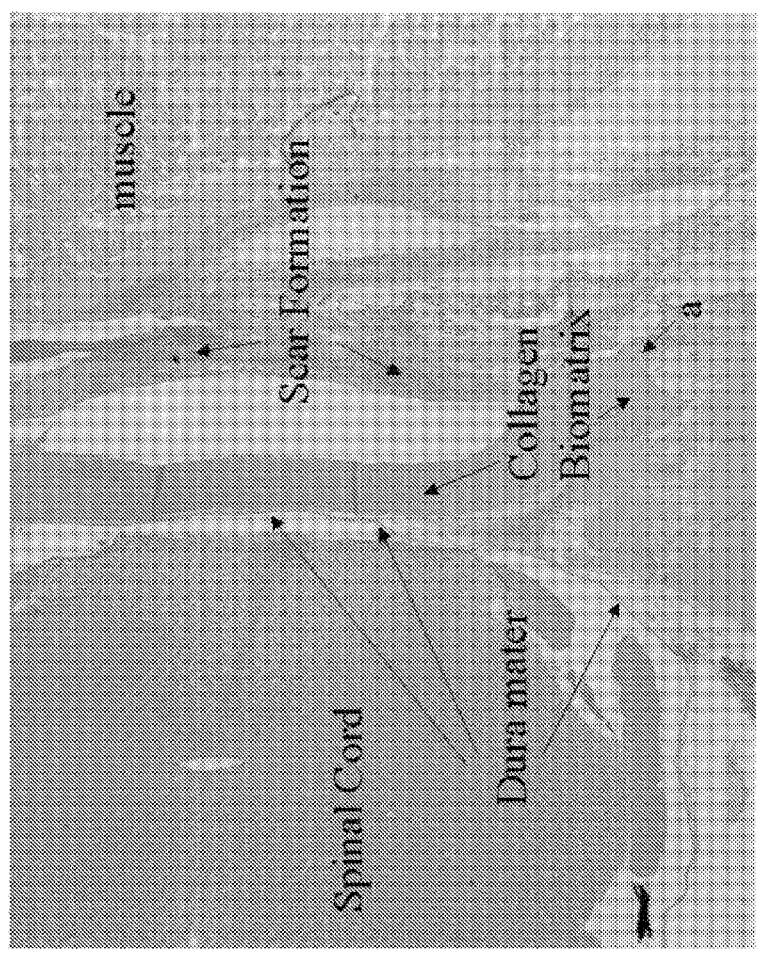
Figure 13E:
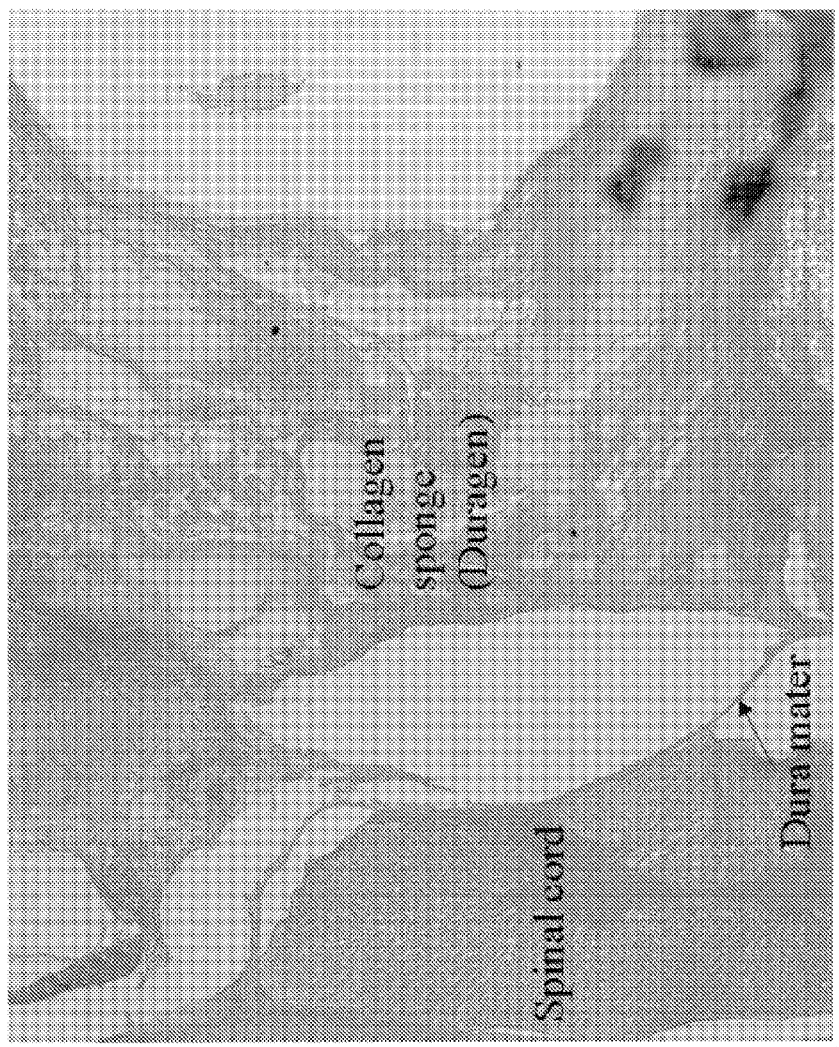

The study shows following histological findings:

Immediately postoperative: The collagen foil biomatrix is placed between the dura mater and the dorsal defect area and forms a biological separation layer between the dura mater and the dorsal wound area. It is not fixed to the tissue of the dorsal defect. Blood (erythrocytes) adhere in a thin layer to the surface of the collagen foil biomatrix and proves its function as a hemostat. The parallel microscopically multilayer structure of the collagen foil biomatrix, which is nonporous and fluid-tight to blood, is clearly visible. The thickness of the collagen foil biomatrix is about 0.3 mm. (FIG. 12)

One week postoperative: The membrane is mostly integrated in the surrounding tissues. There is infiltration of blood cells, especially lymphocytes (FIG. 13 A). The subdural space is free from cell infiltration or adhesion tissue. On the dorsal surface cells are directed along the surface and have hardly penetrated the surface of the collagen foil biomatrix. At the edges of the defect the collagen biomatrix was applied on the bone. The contact area (a) is a preferred area of bioactivity (biomatrix/cell interaction) and the beginning of directed cell infiltration along the multilayer structure. The area between the multilayered collagen foil biomatrix and the dura mater consists of loose tissue containing fat cells (b), comparable to the tissue of the epidural space in areas where the anatomy was not affected by the surgery (c) as shown in FIG. 13 A.

FIG. 13 A shows the contact area between the multilayered collagen foil biomatrix and the bone at the edge of the defect (a). Intensive interaction of cells and the multilayered collagen foil biomatrix. The remodelling of the multilayered collagen foil biomatrix starts with the directed infiltration of cells (fibroblasts, granulocytes) into the parallel multilayer structure of the multilayered collagen foil biomatrix.

FIG. 13 B shows the contact area between the multilayered collagen foil biomatrix and the bone at the edge of the defect (a).

FIG. 13 C shows the multilayered collagen foil biomatrix in the center of the laminectomy defect. The collagen biomatrix is integrated and is separating the ventral epidural space from the dorsal scar formation. Cells are directed along the dorsal surface and have not penetrated the surface of the collagen biomatrix. The area between the collagen biomatrix and the dura mater consists of loose tissue containing fat cells (a).

FIG. 13 D shows a NZW rabbit 1 week postoperative. The multilayered collagen foil biomatrix is closing the laminectomy defect and separating the dura from the beginning cell rich dorsal scar formation. Cells have not penetrated the surface of the collagen biomatrix. At the edge of the collagen biomatrix the beginning of directed infiltration of repair cells into the multilayer structure(a) is seen.

FIG. 13 E shows a NZW rabbit 1 week postoperative. A collagen sponge (DURAGEN) was used to cover the laminectomy defect. In contrast to the present invention, there is no clear nonporous separation layer between the epidural space and the dorsal wound area. The collagen sponge is soaked with blood.

Two weeks postoperative: The integration of the membrane into surrounding tissue is improved by in-growth of capillaries structures. The amount of the lymphocyte, segmented granulocyte is increased. The structure of the collagen foil biomatrix can be distinguished form the surrounding tissue. There is an inflammatory reaction above the membrane with exudation of lymphocyte and granulocyte. The subdural space is free from cell infiltration or adhesion tissue.

Figure 14A:
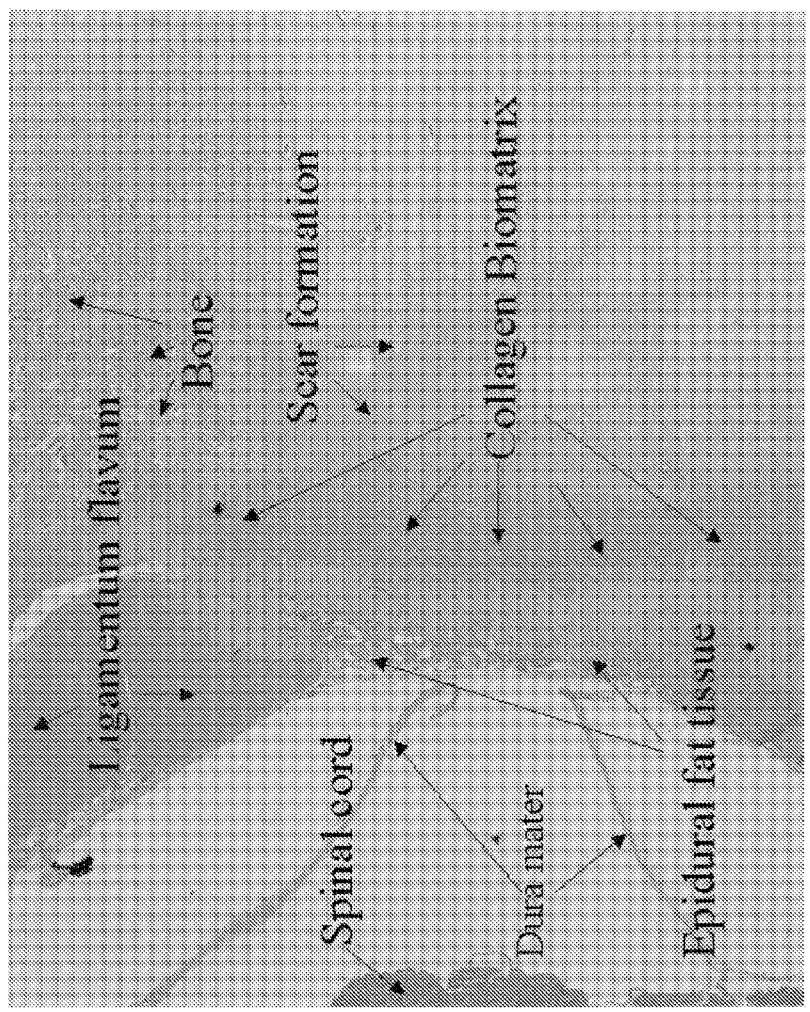
FIG. 14 A shows a rabbit two weeks postoperative; Magnification: ×2.5; HE staining. The multilayered collagen foil biomatrix is fully integrated. Tissue repair cells have infiltrated the collagen biomatrix and the dura mater is separated by loose tissue with fat cells from the scar formation and the remodeled collagen biomatrix.
Figure 14B:
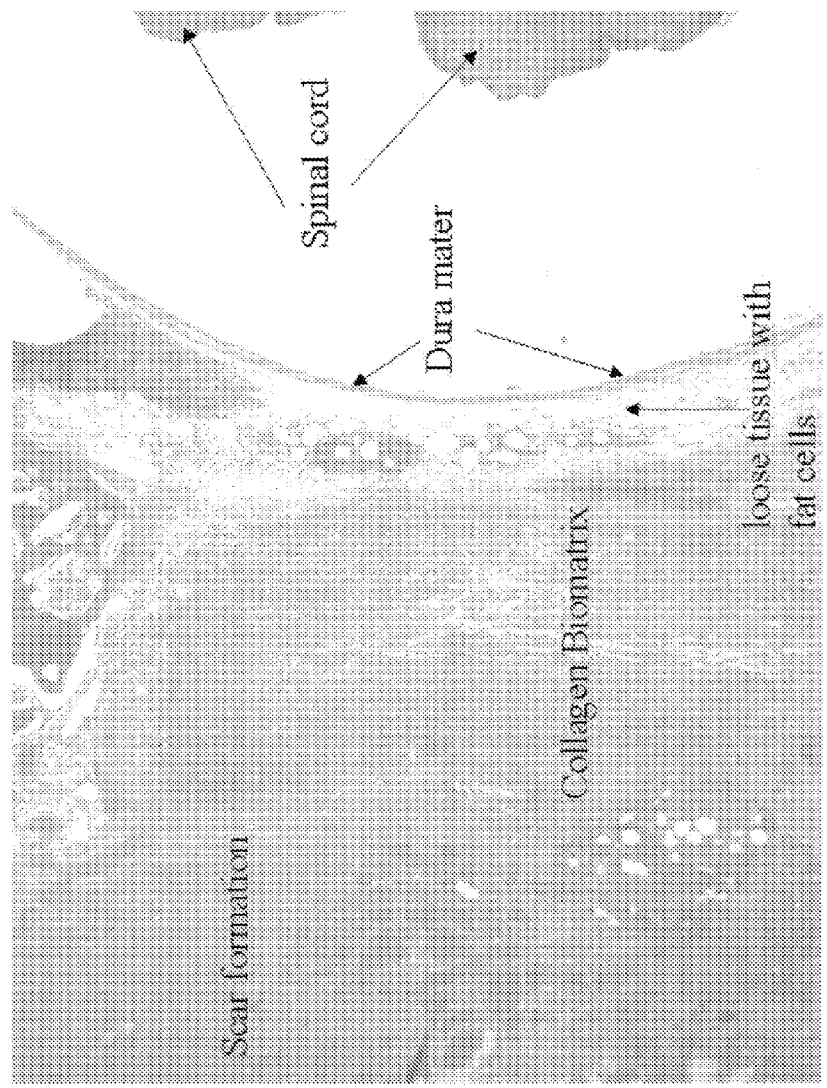
Figure 14C:
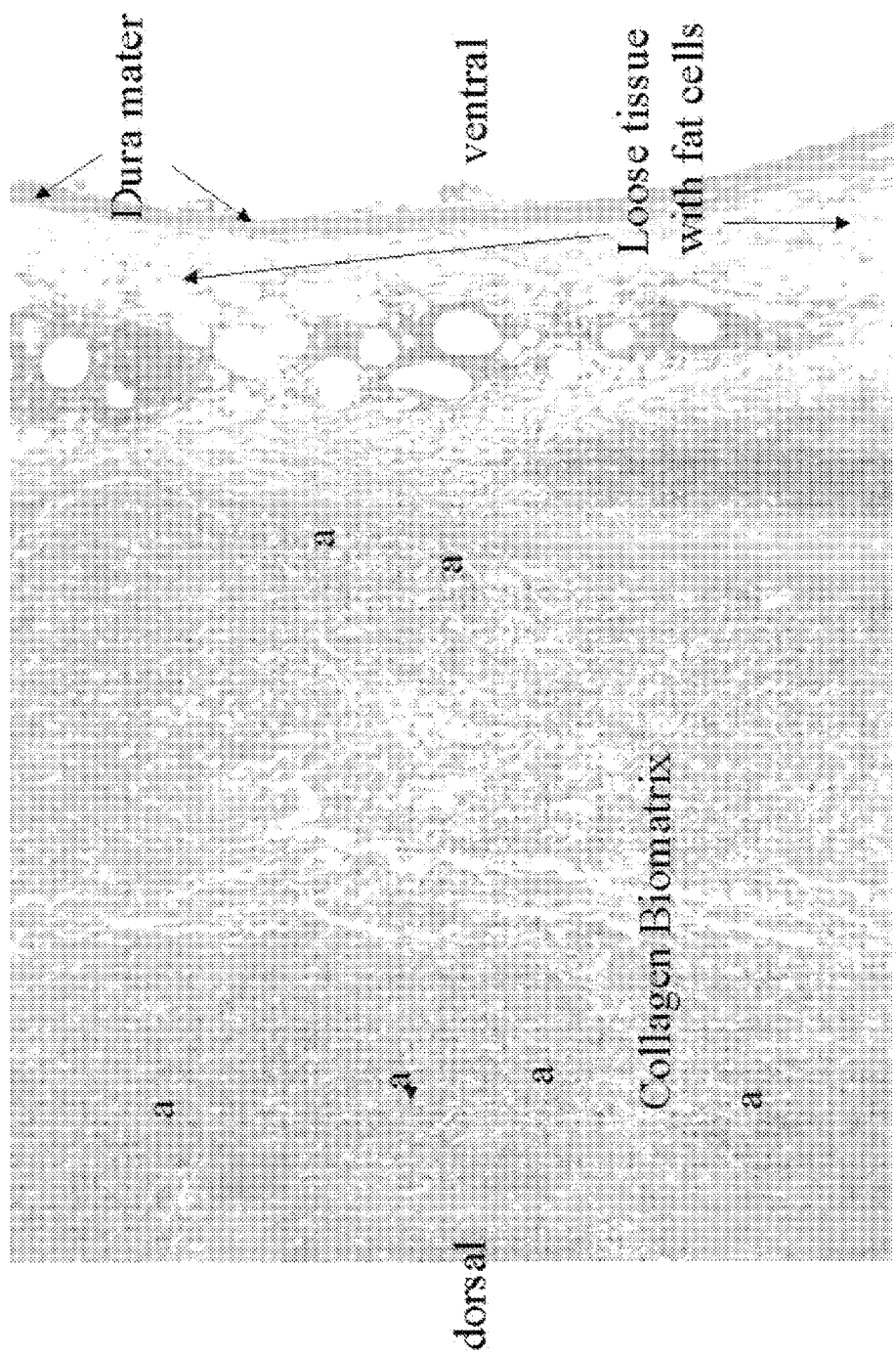

FIGS. 14 A-C show a NZW rabbit two weeks postoperative. The multilayered collagen foil biomatrix is fully integrated. Tissue repair cells have infiltrated the collagen biomatrix and are directed along the multilayer structure. The dura mater is separated by loose tissue with fat cells from the scar formation and the remodeled collagen biomatrix.

CONCLUSIONS

The nonporous multilayered collagen foil biomatrix of the present invention proved to have an immediate and excellent separation and protection function between the dura mater and the dorsal surgical defect, avoiding the uncontrolled distribution of blood, fibrin and necrotic materials into the peridural area and directing and separating the cell growth of the beginning scar above the dorsal surface. The biofunctional collagen foil also directs the cell in-growth into its multilayer structure. The speed of in-growth along the multilayered structure is higher than the in-growth of cells into the biomatrix from the dorsal surface. There is no in-growth of cells in the first week into the ventral surface of the collagen foil biomatrix. The different speed of cell in-growth along or across the multilayered structure is in line with a clinical observation after the peridural implantation of the multilayered collagen foil biomatrix one week postoperative (Ex. II).

After two weeks, the multilayered biomatrix is infiltrated by repair cells. There is a full integration of the biomatrix into the physiological scar formation of the dorsal surgical wound area. The dura mater is separated by a loose fat tissue which looks similar to the fat tissue, which is physiologically separating the dura mater from the spinal canal. There is a high bioactivity of repair cells directed along the gradually disappearing multilayer structure of the cell rich biomatrix. The biomatrix is remodeled and integrated into the normal anatomical structure.

The multilayered collagen foil biomatrix of the present invention proved to be an effective, biocompatible and biofunctional immediate protection and separation layer between the dura mater and the dorsal defect area which is directing the cell in-growth within the multilayer structure and the cell growth above its dorsal surface. By directing the cell growth, the collagen foil biomatrix effectively controls the remodeling and tissue regeneration process and provides optimal conditions for the prevention and minimization of clinically relevant adhesions.

The invention claimed is:

1. A method for directing cell in-growth and controlled tissue regeneration in a tissue comprising covering said tissue present in a mammal with a multilayered collagen foil biomatrix comprising multiple layers of precipitated collagen fibrils that form stacked collagen fibril sheets packed tightly together and comprising pores that are isolated from one another and are not interconnected in a manner which traverses the collagen foil biomatrix and a surface of the collagen foil biomatrix is non-porous, wherein said tissue is selected from the group consisting of spinal column tissue, dura mater, and spinal nerves, wherein said covering of said tissue prevents post-surgical adhesion and fibrosis formation on a surface of said tissue by separating said tissue from adjacent tissues and wherein said covering directs cell ingrowth and controlled tissue regeneration in said tissue.

2. The method of claim 1, wherein the mammal is a human being.

3. The method according to claim 1, wherein the step of covering said tissue with said multilayered collagen foil biomatrix occurs during spinal surgery.

4. The method according to claim 1, wherein the multilayered collagen foil biomatrix attracts cells selected from the group consisting of repair cells and regeneration cells thereby inducing new tissue growth.

5. The method according to claim 1, wherein the multilayered collagen foil biomatrix directs the growth of cells on the surface of the biomatrix and in-growth of cells in the interstices of the multiple layers of the biomatrix, wherein the cells are selected from the group consisting of repair cells and regeneration cells.

6. The method according to claim 5, wherein the multilayered collagen foil biomatrix is reabsorbed and remodeled into natural tissue during the in-growth of cells selected from the group consisting of repair cells and regeneration cells.

7. A method of treating a mammal comprising a defect needing ingrowth of cells or tissue regeneration comprising covering a defect in a tissue selected from the group consisting of spinal cord and dura mater in said mammal with a multilayered collagen foil biomatrix comprising multiple layers of precipitated collagen fibrils that form stacked collagen fibril sheets packed tightly together and comprising pores that are isolated from one another and are not interconnected in a manner which traverses the collagen foil biomatrix, wherein said multilayered collagen foil biomatrix serves as a separation layer between the defect and adjacent tissues, wherein said covering step directs cell ingrowth within the interstices of the multilayered collagen foil biomatrix, and wherein said covering step results in ingrowth of cells or tissue regeneration in said defect thereby treating said mammal.

8. The method according to claim 7, wherein the multilayered collagen foil biomatrix is derived from one of the following sources selected from the group consisting of bovine, porcine, equine, human collagen and mixtures thereof.

9. The method of claim 7, wherein the multilayered collagen foil biomatrix is attached to the defect in said mammal using fibrin sealant.

10. The method of claim 7, wherein the cell in-growth is directed into the interstices between the layers of the multilayered collagen foil biomatrix and on the outer surface of the multilayered collagen foil biomatrix.

11. A method of treating a spinal column tissue in a mammal during a spinal surgery comprising covering the spinal column tissue present in said mammal with a multilayered collagen foil biomatrix comprising multiple layers of precipitated collagen fibrils that form stacked collagen fibril sheets packed tightly together and comprising pores that are isolated from one another and are not interconnected in a manner which traverses the collagen foil biomatrix, wherein said collagen fibrils are selected from the group consisting of bovine, porcine, equine, human collagen fibrils and mixtures thereof, wherein said covering step directs cell ingrowth within the interstices of the multilayered collagen foil biomatrix, wherein said covering step prevents adhesions, and wherein said covering step results in treatment of said spinal column tissue in said mammal during spinal surgery.

12. The method of claim 11, wherein the adhesions are post-operative adhesions, adhesions caused by trauma, peridural adhesions, or perineural adhesions.

13. The method of claim 11 wherein the multilayered collagen foil biomatrix directs cell growth between the interstices of the layers and on the surface of the multilayered collagen foil biomatrix.

14. The method of claim 11, where the multilayered collagen foil matrix creates a primary liquid-tight seal and separation layer between said tissue and adjacent tissues.

15. The method of claim 14, wherein the multilayered collagen foil biomatrix is smooth and the surface of the multilayered collagen foil biomatrix is non-porous.

16. The method of claim 11 wherein the multilayered collagen foil biomatrix is reabsorbed and remodeled into natural tissues.

17. The method of claim 16 wherein the multilayered foil biomatrix is reabsorbed and remodeled into natural tissues in 14 days.

18. The method of claim 11, wherein the collagen fibrils are equine collagen fibrils.

19. The method of claim 11, wherein the multilayered collagen foil biomatrix is obtained in kit form prior to the covering step.

20. The method of claim 11, further comprising applying an anti-adhesion product to a surface of the multilayered collagen foil biomatrix.

21. The method of claim 20, wherein the anti-adhesion product comprises polyethylene glycol (PEG).

22. The method of claim 20, wherein the anti-adhesion product is applied to one surface of the multilayered collagen foil biomatrix.

23. The method of claim 1, wherein the thickness of the multilayered collagen foil biomatrix increases up to about 6 times its dry thickness when it is completely hydrated.

24. The method of claim 1, wherein the precipitated collagen fibrils are arranged in a multi-directional fashion in the plane of each stacked collagen fibril sheet.

25. The method of claim 7, wherein the precipitated collagen fibrils are arranged in a multi-directional fashion in the plane of each stacked collagen fibril sheet.

26. The method of claim 11, wherein the precipitated collagen fibrils are arranged in a multi-directional fashion in the plane of each stacked collagen fibril sheet.

* * * * *